(12) United States Patent
Elia et al.

(10) Patent No.: US 10,750,991 B2
(45) Date of Patent: Aug. 25, 2020

(54) SYSTEMS AND METHODS FOR ANALYZING REFLECTIONS OF AN ELECTRICAL SIGNAL FOR PERFORMING MEASUREMENTS

(71) Applicant: ART Medical Ltd., Netanya (IL)

(72) Inventors: Liron Elia, Kiryat-Ata (IL); Gavriel J. Iddan, Haifa (IL)

(73) Assignee: ART Medical Ltd., Netanya (IL)

( * ) Notice: Subject to any disclaimer, the term of this patent is extended or adjusted under 35 U.S.C. 154(b) by 0 days.

(21) Appl. No.: 16/181,501

(22) Filed: Nov. 6, 2018

(65) Prior Publication Data

US 2019/0133512 A1    May 9, 2019

Related U.S. Application Data

(60) Provisional application No. 62/581,921, filed on Nov. 6, 2017.

(51) Int. Cl.
*A61B 5/00* (2006.01)
*A61B 5/053* (2006.01)

(52) U.S. Cl.
CPC .......... *A61B 5/4211* (2013.01); *A61B 5/0538* (2013.01); *A61B 5/4233* (2013.01); *A61B 5/687* (2013.01); *A61B 5/7257* (2013.01)

(58) Field of Classification Search
CPC .................................................... A61B 5/0537
See application file for complete search history.

(56) References Cited

U.S. PATENT DOCUMENTS

2012/0016256 A1* 1/2012 Mabary ............... A61B 5/0538
  600/547
2012/0078074 A1    3/2012 Gao et al.
(Continued)

FOREIGN PATENT DOCUMENTS

| WO | WO 2014/016765 | 1/2014 |
| WO | WO 2015/017837 | 2/2015 |
| WO | WO 2016/187456 | 11/2016 |

OTHER PUBLICATIONS

European Search Report and the European Search Opinion dated Apr. 1, 2019 From the European Patent Office Re. Application No. 18204747.2. (6 Pages).

*Primary Examiner* — Daniel L Cerioni
*Assistant Examiner* — Yasmeen S Warsi

(57) ABSTRACT

There is provided a system for measuring impedance at multiple locations within a body of a patient, comprising: an elongated probe sized and shaped for being disposed within a cavity of the body of the patient or in an extracorporeal position, at least one pair of parallel transmission wires disposed along a length of the elongated probe, a plurality of impedance elements, each connected to the at least one pair of parallel transmission wires at a respective spaced apart location along the length of the elongated probe in a ladder arrangement, a transmitter configured for injecting an electrical signal to the at least one pair of parallel transmission wires, a receiver configured for measuring a plurality of reflections of the electrical signal from the plurality of impedance elements, and a processor configured for computing an impedance value for each of the impedance elements according to the measured plurality of reflections.

23 Claims, 14 Drawing Sheets

(56) References Cited

U.S. PATENT DOCUMENTS

| | | | |
|---|---|---|---|
| 2013/0190646 A1* | 7/2013 | Weinstein | A61B 5/0028 600/547 |
| 2013/0310673 A1* | 11/2013 | Govari | A61B 5/036 600/373 |
| 2014/0020473 A1 | 1/2014 | Ricotti et al. | |

* cited by examiner

Numerical calculation example

Assume the following values: ($V_p = 1[V]$) pulse propagation velocity 10 cm/nsec $Z_0 = 500\,\Omega$    $Z_1 = 1000\,\Omega$    $Z_2 = 1000\,\Omega$    $Z_3 = 350\,\Omega$    $Z_4 = 50\,\Omega$ Reflection coef.    $\rho_1 = 0.33$    $\rho_2 = 0.33$    $\rho_3 = -0.18$    $\rho_4 = 0.64$ Transmission coef.    $\tau_1 = 0.67$    $\tau_2 = 0.67$    $\tau_3 = 0.824$    $\tau_3 = 0.66$ Net reflection coef.    $r_1 = \rho_1$    $r_2 = \rho_2\,\tau_1^2$    $r_3 = \rho_3\,\tau_1^2\,\tau_2^2$    $r_4 = \rho_4\,\tau_1^2\,\tau_2^2\,\tau_3^2$ Reflected pulse amp.    $V1 = 0.33[V]$    $V2 = 0.15[V]$    $V3 = -0.03[V]$    $V4 = -0.085[V]$

FIG. 15

SYSTEMS AND METHODS FOR ANALYZING REFLECTIONS OF AN ELECTRICAL SIGNAL FOR PERFORMING MEASUREMENTS

RELATED APPLICATION(S)

This application claims the benefit of priority under 35 USC § 119(e) of U.S. Provisional Patent Application No. 62/581,921 filed on Nov. 6, 2017, the contents of which are incorporated by reference as if fully set forth herein in their entirety.

FIELD AND BACKGROUND OF THE INVENTION

The present invention, in some embodiments thereof, relates to performing measurements and, more specifically, but not exclusively, to systems and methods for analyzing electrical signals for performing measurements on or in a body of a patient.

Electrical signals are commonly generated and senses for performing measurements of different parameters within a body of a patient. For example, bioimpedance sensing (BIS) is commonly performed as part of different medical procedures for estimating composition of the body. Impedance measurements may be performed from within the body, or via electrodes placed on the surface of the skin. Improvements to medical devices that perform electrical signal-based measurements are sought.

SUMMARY OF THE INVENTION

According to a first aspect, a system for measuring impedance at a plurality of locations within a body of a patient, comprises: an elongated probe sized and shaped for being disposed within a cavity of the body of the patient or in an extracorporeal position, at least one pair of parallel transmission wires disposed along a length of the elongated probe, a plurality of impedance elements, each connected to the at least one pair of parallel transmission wires at a respective spaced apart location along the length of the elongated probe in a ladder arrangement, a transmitter configured for injecting an electrical signal to the at least one pair of parallel transmission wires, a receiver configured for measuring a plurality of reflections of the electrical signal from the plurality of impedance elements, and a processor configured for computing an impedance value for each of the impedance elements according to the measured plurality of reflections.

According to a second aspect, a system for measuring impedance at a plurality of locations within a body of a patient, comprises: an elongated probe sized and shaped for being disposed within a cavity of the body of the patient or in an extracorporeal position, at least one pair of parallel transmission wires disposed along a length of the elongated probe, wherein the pair of parallel transmission wires are alternatively electrical insulated and electrically non-insulated to create spaced apart pairs of non-insulated wire portions, a transmitter configured for injecting an electrical signal to the pair of parallel transmission wires, a receiver configured for measuring a reflection of the electrical signal from each of the plurality of pairs of non-insulated wire portions, and a processor configured for computing an impedance value for each of the plurality of pairs of non-insulated wire portions.

According to a third aspect, a method of measuring impedance at a plurality of locations within a body of a patient, comprises: injecting an electrical signal to a pair of parallel transmission wires disposed along a length of a elongated probe sized and shaped for being disposed within a cavity of a body of a patient or in an extracorporeal position, measuring a plurality of reflections of the electrical signal from each of a plurality of impedance disturbances contacting the pair of parallel transmission wires at a respective spaced apart locations along the length of the elongated probe in a ladder arrangement, wherein said plurality of impedance disturbances selected from the group consisting of: solid, tissue, biochemical composition and liquid, and computing an impedance value for each of the impedance disturbances according to the measured plurality of reflections.

At least some of the systems, apparatus, methods, and/or code instructions described herein address the technical problem of sensing impedance values at a large number of locations within a cavity of a body of a patient. Intra-body procedures may include performing measurement of impedance values within a body of a patient, for example, within a cavity of the body of a patient. Standard medical equipment performs impedance measurements attaching conductors to each of the impedance sensing elements. Earlier extra corporal measurements are an example of an additional option with conductors and electrodes mounted on a strip of flexible PCB. The impedance measurements are then carried out by multiplexing each conductor corresponding to a respective impedance sensing element at a time and performing the needed measurement by standard impedance sensing methods such as forcing a known current $I(\omega)$ of known frequency into the impedance element and measuring the resulting voltage drop $V(\omega)$. The impedance is computed by:

$$Z(\omega) = \frac{V(\omega)}{I(\omega)}$$

The technical problem arises when a large number of impedance elements are used to measure a large number of impedance values at different locations. For example, devices to perform BIS are based on connecting multiple individual electrodes by conductors to an electronic processing unit which requires heavy cabling when multiple sensing points and associates electrodes are desired. The large number of electrodes require a large number of conductors and/or large total cross section of cabling which place a physical limit on the design of a catheter housing the large number of conductors and impedance elements. For example, the number of impedance elements may need to be reduced, resulting in less accurate coverage of a cavity since the impedance elements may need to be relatively far apart from one another, and do not provide coverage between the elements. In another example, the large number of impedance elements may create a bulky catheter due to the large number of conductors, which may limit the use of such catheter. At least some of the systems, apparatus, methods, and/or code instructions described herein provide a technical solution to the technical problem by using as little as two conducting wires (referred to herein as a pair of transmission lines) that are used to sense impedance at a larger number of locations. The two conducting wires provide high resolution of impedance measurements.

At least some of the systems, apparatus, methods, and/or code instructions described herein improve the technology of sensing impedance values within a body of a patient via a catheter, in terms of resolution of the measured impedance values, and/or in terms of the ability to compute the location along the catheter corresponding to a selected impedance value. The higher resolution of the measured impedance values along a cavity of a body of the patient reduces errors in measurement by reducing regions along the cavity where no impedance values are measured. The ability to compute the location of a certain measured impedance value is improved by the high resolution of the measurements. Therefore, the precise location where target impedance values are obtained may be computed, for example, a defined distance and/or range along a catheter.

At least some of the systems, apparatus, methods, and/or code instructions described herein improve the technology of enteral feeding of a patient using an enteral feeding tube. The ability to use pairs of transmission wires to measure impedance values at multiple locations along the length of the feeding tube allows for the feeding tube to be made with a relatively smaller diameter, even when having a large number of impedance values are measured along its length. The smaller diameter tube is easier to insert into the patient, in particular easier to insert into babies and patients in which insertion of the tube is generally difficult (e.g., due to anatomical abnormalities). The ability to sense impedance values at multiple locations along the feeding tube at a high resolution provides for high resolution monitoring of reflux within the esophagus. The amount of the reflux and/or location of the reflux along the esophagus may be detected and monitored with high resolution by the multiple impedance elements. The ability to compute the location of selected impedance values along the feeding tube may provide for high resolution monitoring of the amount and/or location of the reflux correspond to different locations along the feeding tube. For example, to track how far up the esophagus reflux has reached (e.g., determine and/or monitoring increasing risk of aspiration) and/or track the decrease in the level of reflux in the esophagus (e.g., track the decreasing risk of aspiration). The high resolution impedance sensing along the tube may in addition improve the tube localization vs. the LES for example which is an important part of ICU patients feeding.

In a further implementation form of the first, second, and third aspects, the processor is configured for establishing an impedance value baseline for each of the plurality of impedance elements according to the respective computed impedance value, the transmitter is configured for sequentially injecting the electrical signal and the receiver is configured for iteratively measuring the plurality of reflections of the electrical signals by the plurality of impedance elements, and the processor is configured for monitoring for changes relative to the baseline of each of the plurality of impedance elements.

In a further implementation form of the first, second, and third aspects, the elongated probe comprises a naso/orogastric tube for being disposed within the esophagus of the patient so that at least a distal end thereof is in the stomach lumen of a patient while at least one segment thereof is in the esophagus, wherein the naso/orogastric tube includes at least one feeding channel for conducting a feeding content within at least one feeding opening located in the distal end, wherein the processor is configured for at least one of: (i) monitoring for impedance values indicative of reflux in the esophagus, (ii) monitoring for impedance values indicative of displacement of the naso/orogastric tube within the esophagus and tracking location of the naso/orogastric tube, (iii) generating instructions for execution by an enteral feeding controller for pausing of the enteral feeding when the impedance values indicative of reflux in the esophagus are detected.

In a further implementation form of the first, second, and third aspects, the injected signal comprises a reference harmonic signal having a selected frequency, and the processor is configured for computing the impedance value for each of the impedance elements according to a frequency domain analysis of the plurality of reflections.

In a further implementation form of the first, second, and third aspects, the reference harmonic signal is a sinusoidal wave.

In a further implementation form of the first, second, and third aspects, measuring the plurality of reflections of the electrical signal from each of the plurality of impedance elements comprises mixing the plurality of reflections with a complement of the injected reference harmonic signal for eliminating or significantly reducing a radiofrequency (RF) component to identify the intermediate frequency (IF) component which is a function of one of the measured impedance values corresponding to a selected impedance element, and computing an inversion of the IF component to compute the impedance value corresponding to the selected impedance element.

In a further implementation form of the first, second, and third aspects, the selected impedance element is identified according to an analysis of a phase shift of the plurality of reflections relative to the electrical signals, the phase shift being a function of a location of the selected impedance element.

In a further implementation form of the first, second, and third aspects, the mixing the plurality of reflections with the reference harmonic signal is iterated for each reference harmonic signal corresponding to one of a plurality of injected signal frequencies and corresponding to each of the plurality of impedance elements, to compute the impedance value corresponding to each respective impedance element.

In a further implementation form of the first, second, and third aspects, the IF component denotes a Discrete Fourier Transform (DFT) of the reflected signal, and wherein the reflected signal is computed by computing an Inverse Discrete Fourier Transform (IDFT) of the IF component.

In a further implementation form of the first, second, and third aspects, measuring the plurality of reflections of the electrical signal from each of the plurality of impedance elements comprises computing a spectral response of the plurality of impedance elements to each one of a plurality of harmonic injected signals each having a respective frequency, and computing an inverse of the spectral response.

In a further implementation form of the first, second, and third aspects, the injected electrical signal comprises a single pulse of a selected pulse width, and the processor is configured for computing the impedance value for each of the impedance elements according to a time domain analysis of the plurality of reflections.

In a further implementation form of the first, second, and third aspects, measuring comprises measuring a sequence of reflected time spaced pulses denoting reflections of the single pulse from each of the plurality of impedance element.

In a further implementation form of the first, second, and third aspects, the receiver is configured for selecting one reflected signal from the sequence of reflected time spaced pulses corresponding to a certain impedance element, wherein the impedance value is computed for the certain impedance element corresponding to the selected reflected signal, wherein the selected reflected signal is selected by a timing gate according to a computed delay corresponding to an estimated amount of time for the single pulse to travel to the certain impedance element and for the selected reflected signal to travel back to a receiver, wherein the impedance value is estimated based on the selected reflected signal.

In a further implementation form of the first, second, and third aspects, the single pulse is sequentially injected, and wherein during each iteration reflected signal is selected corresponding to the certain impedance element and integrated to compute a built-up signal, wherein the impedance value of the certain impedance element is computed according to the built-up signal.

In a further implementation form of the first, second, and third aspects, the plurality of impedance elements are electrically un-insulated, and portions of the parallel transmission wires located between the plurality of impedance elements are electrically insulated.

In a further implementation form of the first, second, and third aspects, the elongate probe includes a plurality of recesses each extending within a wall thereof and corresponding to one of the plurality of impedance elements.

In a further implementation form of the first, second, and third aspects, the processor is further configured for establishing an impedance value baseline for each of the plurality of pairs of non-insulated wire portions according to the respective computed impedance values, and the transmitter is configured for iteratively injecting the electrical signal and the receiver is configured for iteratively measuring the reflection of the electrical signal from each of the plurality of pairs of non-insulated wire portions, and the processor is configured for monitoring for statistically significant changes relative to the baseline of each of the plurality of pairs of non-insulated wire portions.

In a further implementation form of the first, second, and third aspects, the pair of parallel transmission wires are embedded within a wall of the elongated probe, and the elongated probe further comprises a recess extending within the wall of the elongated probe corresponding to each pair of non-insulated wire portions, wherein both non-insulated wire portions of each pair reside in a respective single common recess, wherein portion of the pair of parallel transmission wires located between recesses are insulated by the wall of the elongated probe.

In a further implementation form of the first, second, and third aspects, the processor is configured for monitoring for impedance values indicative of body fluid and/or tissue contacting both non-insulated wire portions of at least one pair.

In a further implementation form of the first, second, and third aspects, the pair of parallel transmission wires are disposed on an outer surface of the elongated probe, wherein the pair of parallel transmission wires are coated with electrically insulating material at spaced apart locations, wherein regions of the pair of parallel transmission wires not coated with the electrically insulating material denote the spaced apart pairs of non-insulated wire portions.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 15 is a table depicting computation of the impedance values based on the reflected pulses, for the prophetic experimental set-up of FIG. 14, in accordance with some embodiments of the present invention.

DETAILED DESCRIPTION OF SPECIFIC EMBODIMENTS OF THE INVENTION

Figure 1:
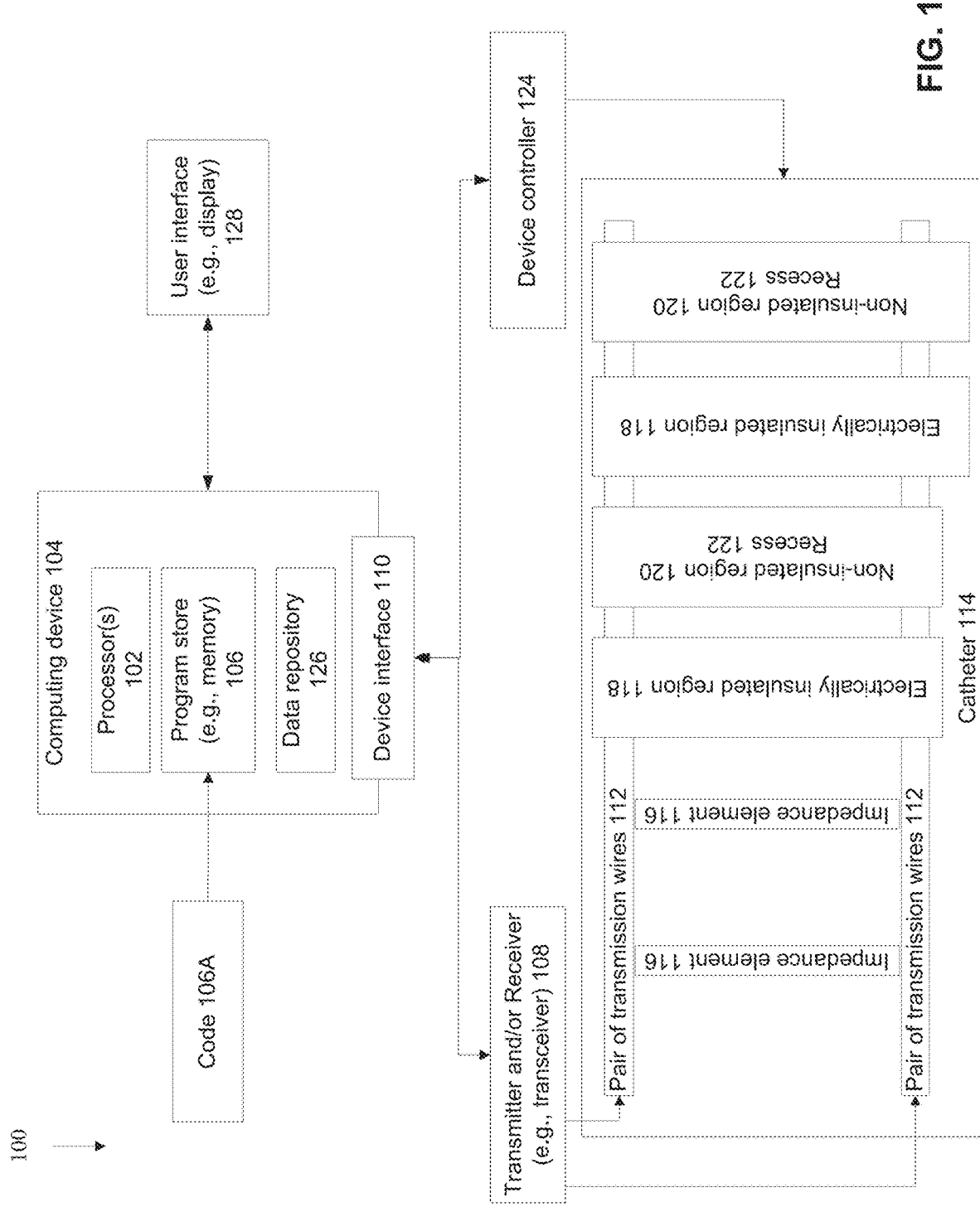
FIG. 1 is a schematic of a system for measuring impedance at multiple locations within a body of a patient, in accordance with some embodiments of the invention.

The present invention, in some embodiments thereof, relates to medical devices for performing measurements and, more specifically, but not exclusively, to systems and methods for analyzing electrical signal(s) for performing measurements on or in a body of a patient.

As used herein, the term disturbance impedance (or impedance disturbance) may be interchanged and/or refer to impedance elements and/or non-insulated portions of the pair of transmission wires which are electrically connected, for example, by the presence of fluid (e.g., reflux) and/or tissue (e.g., inner wall of a cavity and/or lumen) and/or solid (e.g., solid impedance elements components connecting the two wire). The term impedance element may sometimes refer to, and/or be interchanged with, the term non-insulated portions of the pair of transmission wires. It is noted that the non-insulated portions of the pair of transmission wires may act as impedance elements (i.e., be associated with a measurable impedance value) when electrical connectivity is formed between the non-insulated wires, for example, when fluid (e.g., reflux) is present between the pair of non-insulated wire portions, and/or when both wires contact tissue.

An aspect of some embodiments of the present invention relates to a system, an apparatus, a method, and/or code instructions (stored on a memory, executable by hardware processors) for measuring impedance at multiple locations within a body of a patient by injection of an electrical signal into a pair of parallel transmission wires, and measuring reflections by each one of multiple, spaced apart impedance elements located along the length of the parallel transmission wires. The parallel transmission wires and impedance elements are located on a catheter that is sized and shaped for being disposed within a cavity and/or placed in an extracorporeal position on the body of the patient, for example, a naso/orogastric tube, an endotracheal tube, a urinary catheter, positioned on the skin, positioned on the extremities of the body (e.g., on the leg, on the arm, on the stomach, on the back, along the spine) vascular catheter, including other options for mounting conductors and/or electrodes such as flexible printed circuit board (PCB). A transmitter injects the electrical signal to the pair of parallel transmission wires (e.g., proximal end thereof), and a receiver measures multiple reflections from each of the impedance elements (e.g., at the same proximal end). The reflections are analyzed to compute impedance values for each of the impedance elements, for example, based on a computation performed for transmission lines.

An aspect of some embodiments of the present invention relates to a system, an apparatus, a method, and/or code instructions (stored on a memory, executable by hardware processors) for measuring impedance at multiple locations within a body of a patient by injection of an electrical signal into a pair of parallel transmission wires that are alternating electrically insulated and electrically non-insulated. Spaced apart pairs of non-insulated portions (e.g., "windows") of the pair of parallel transmission wires act as impedance elements when fluid and/or tissue provides electrical connectivity between the respective pair of un-insulated parallel transmission wires. The parallel transmission wires are located on a catheter (and/or a flexible PCB strip) that is sized and shaped for being disposed within a cavity of the body of the patient and/or for being disposed on an extracorporeal location, for example, a naso/orogastric tube, an endotracheal tube, a urinary catheter, a vascular catheter, and a carrier placed on an extremity of the patient and/or on the torso of the patient. A transmitter injects the electrical signal to the (optionally proximal end of the) pair of parallel transmission wires, and a receiver measures multiple reflections from each of the pairs of un-insulated wire portions i.e., the windows. The reflections are analyzed to compute impedance values for each of the pairs of un-insulated wire portions.

As used herein, the term catheter may refer to a flexible PCB strip, and/or other elongated probes sized and shaped for insertion into a cavity of a body of a patient.

Optionally, a baseline impedance value may be established for each of impedance elements and/or the pairs of un-insulated wire portions. The transmitter may iteratively inject additional electrical signals, and the receiver may iteratively measure the reflections from each of the impedance elements and/or pairs of un-insulated wire portions. A processor(s) may monitor for statistically significant changes relative to the baseline of each of the impedance elements and/or pairs of un-insulated wire portions. Statistically significant changes from baseline are indicative of, for example, displacement of the catheter (e.g., forward and/or reverse), contact with the inner tissue wall, and the presence of body fluid (e.g., reflux).

Optionally, a pulse, such as a single pulse is injected into the transmission lines. Multiple reflections of the pulse are received, where each reflection is from another of the impedance disturbances. Pulses from the multiple reflections may be selected according to an estimated delay corresponding to the amount of time taken for the injected pulse to travel to the respective impedance disturbance and arrive back at a receiver. The impedance value may be computed for each impedance disturbance according to the selected reflected pulse corresponding to the respective impedance disturbance. The injection of the pulse and processing and/or analysis of the sequence of reflections of the pulse is sometimes referred to herein as "the time domain approach" since computations are performed in a time domain.

Alternatively, a harmonic signal at a selected frequency is injected into the transmission lines, for example, a sinusoidal wave. A mix of reflected waves is received, each wave is a reflection of the harmonic signal from a different impedance disturbance. A reference signal corresponding to the injected harmonic signal is mixed (e.g., multiplied) with the mix of reflected waves for reducing and/or eliminating the radiofrequency (RF) component, for extraction of the intermediate frequency (IF) component. The IF component is a function of one of the impedance disturbances. The impedance value of the respective impedance disturbance is computed according to the IF component. The injection of the harmonic signal and processing and/or analysis of the mix of reflected waves is sometimes referred to herein as the "frequency domain approach" since computations are performed in a frequency domain.

At least some of the systems, apparatus, methods, and/or code instructions described herein address the technical problem of sensing impedance values at a large number of locations within a cavity of a body of a patient. Intra-body procedures may include performing measurement of impedance values within a body of a patient, for example, within a cavity of the body of a patient. Standard medical equipment performs impedance measurements attaching conductors to each of the impedance sensing elements. Earlier extra corporal measurements are an example of an additional option with conductors and electrodes mounted on a strip of flexible PCB. The impedance measurements are then carried out by multiplexing each conductor corresponding to a respective impedance sensing element at a time and performing the needed measurement by standard impedance sensing methods such as forcing a known current $I(\omega)$ of known frequency into the impedance element and measuring the resulting voltage drop $V(\omega)$. The impedance is computed by:

$$Z(\omega) = \frac{V(\omega)}{I(\omega)}$$

The technical problem arises when a large number of impedance elements are used to measure a large number of impedance values at different locations. For example, devices to perform BIS are based on connecting multiple individual electrodes by conductors to an electronic processing unit which requires heavy cabling when multiple sensing points and associates electrodes are desired. The large number of electrodes require a large number of conductors and/or large total cross section of cabling which place a physical limit on the design of a catheter housing the large number of conductors and impedance elements. For example, the number of impedance elements may need to be reduced, resulting in less accurate coverage of a cavity since the impedance elements may need to be relatively far apart from one another, and do not provide coverage between the elements. In another example, the large number of impedance elements may create a bulky catheter due to the large number of conductors, which may limit the use of such catheter. At least some of the systems, apparatus, methods, and/or code instructions described herein provide a technical solution to the technical problem by using as little as two conducting wires (referred to herein as a pair of transmission lines) that are used to sense impedance at a larger number of locations. The two conducting wires provide high resolution of impedance measurements.

At least some of the systems, apparatus, methods, and/or code instructions described herein improve the technology of sensing impedance values within a body of a patient via a catheter, in terms of resolution of the measured impedance values, and/or in terms of the ability to compute the location along the catheter corresponding to a selected impedance value. The higher resolution of the measured impedance values along a cavity of a body of the patient reduces errors in measurement by reducing regions along the cavity where no impedance values are measured. The ability to compute the location of a certain measured impedance value is improved by the high resolution of the measurements. Therefore, the precise location where target impedance values are obtained may be computed, for example, a defined distance and/or range along a catheter.

At least some of the systems, apparatus, methods, and/or code instructions described herein improve the technology of enteral feeding of a patient using an enteral feeding tube. The ability to use pairs of transmission wires to measure impedance values at multiple locations along the length of the feeding tube allows for the feeding tube to be made with a relatively smaller diameter, even when having a large number of impedance values are measured along its length. The smaller diameter tube is easier to insert into the patient, in particular easier to insert into babies and patients in which insertion of the tube is generally difficult (e.g., due to anatomical abnormalities). The ability to sense impedance values at multiple locations along the feeding tube at a high resolution provides for high resolution monitoring of reflux within the esophagus. The amount of the reflux and/or location of the reflux along the esophagus may be detected and monitored with high resolution by the multiple impedance elements. The ability to compute the location of selected impedance values along the feeding tube may provide for high resolution monitoring of the amount and/or location of the reflux correspond to different locations along the feeding tube. For example, to track how far up the esophagus reflux has reached (e.g., determine and/or monitoring increasing risk of aspiration) and/or track the decrease in the level of reflux in the esophagus (e.g., track the decreasing risk of aspiration). The high resolution impedance sensing along the tube may in addition improve the tube localization vs. the LES for example which is an important part of ICU patients feeding.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
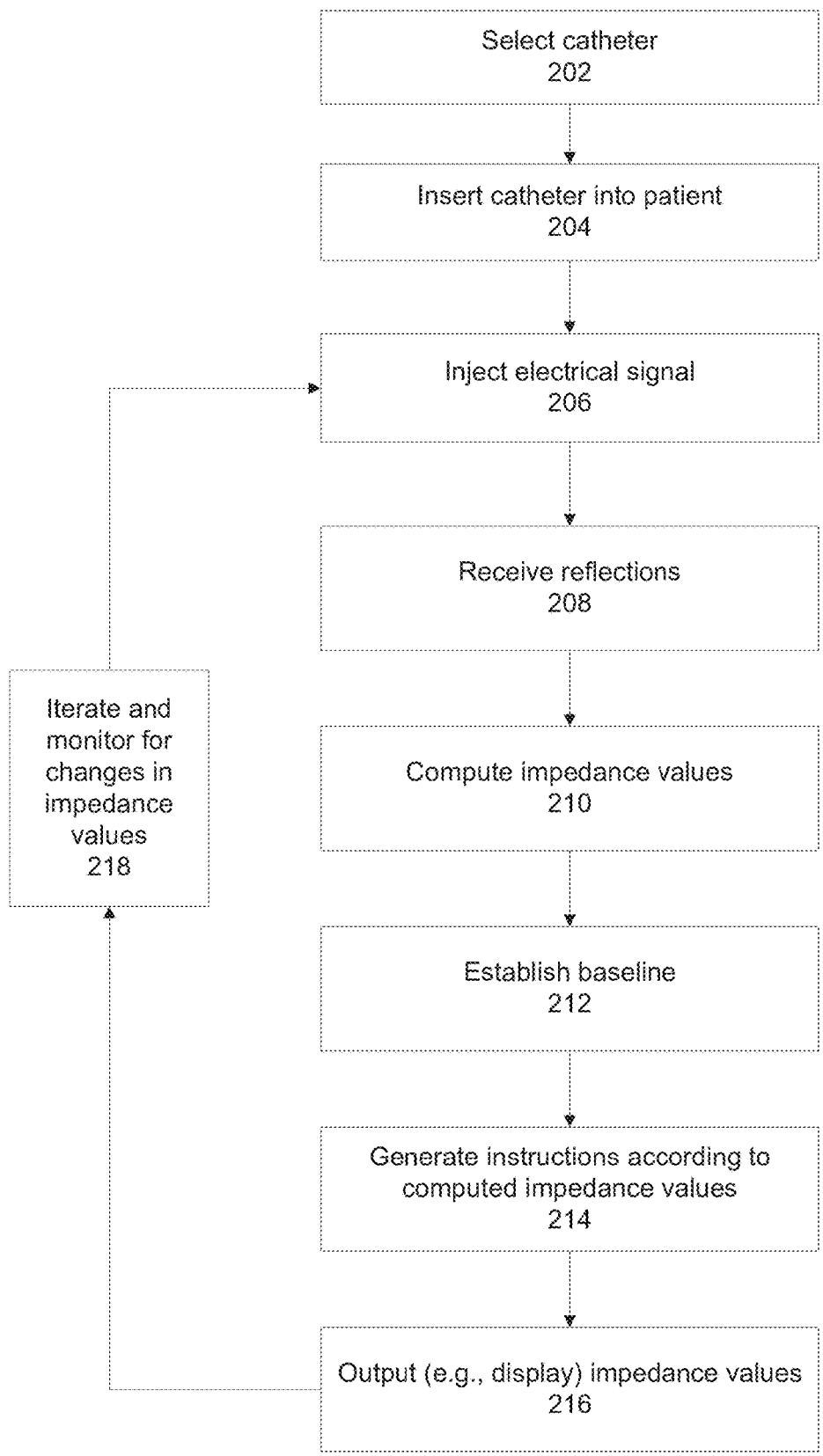
FIG. 2 is a flowchart of a computer implemented method for measuring impedance at multiple locations within a body of a patient, in accordance with some embodiments of the invention.

Reference is now made to FIG. 1, which is a schematic of a system 100 for measuring impedance at multiple locations within a body of a patient, in accordance with some embodiments of the invention. Reference is also made to FIG. 2, which is a flowchart of a computer implemented method for measuring impedance at multiple locations within a body of a patient, in accordance with some embodiments of the invention. One or more acts of the method described with reference to FIG. 2 may be implemented by components of system 100, as described herein, for example, by a processor(s) 102 of a computing device 104 executing code instructions 106A stored in a program store (e.g., memory) 106.

Computing device 104 is in electrical communication with a transceiver 108 (e.g., combined transmitter and receiver components, or separate transmitter and receiver components 108) that generates electrical signals (e.g., pulses and/or harmonic waves) for injection, as described herein, and receives reflections of the injected signals. Exemplary implementations of transceiver 108 are described herein. Computing device 104 generates instructions for operating transceiver 108, and receives data from transceiver 108, optionally via a device interface 110.

Transceiver 108 (and/or transmitter and/or receiver components) may be integrated with computing device 104.

Transceiver 108 is electrically coupled to one or more pairs of parallel transmission wires 112. It is noted that the wires may be approximately parallel to one another while still being referred to herein as parallel, with variations along the length of the catheter in the distance between the wires. Wires 112 are made from an electrically conductive material. Parallel transmission wires 112 are located along a length of a catheter 114 sized and shaped for being disposed within a cavity of a body of a patient and/or for being disposed on an extracorporeal location on the surface of the body of the patient, for example, a naso/orogastric tube for insertion into the esophagus with distal end in the stomach, an endotracheal tube for insertion into the trachea, a urinary catheter for insertion into the bladder, a vascular catheter for insertion into the vasculature such as into the heart and/or blood vessels, and a carrier for positioning on the skin of the patient (e.g., along the arm, along the leg, along the spine, on the stomach, on the chest). There may be one or more pairs of parallel transmission wires 112 located on the outer surface of catheter 114, for example, four pairs, where each pair is located within a 90 degree portion of the outer diameter of the catheter 114, or three pairs where each pair is located within a 120 degree portion of the outer diameter of catheter 114.

Optionally, multiple impedance elements 116 are spaced apart and located along the length of catheter 114, where one end of the respective impedance element 116 is connected to one of the pair of transmission wires 112, and another end of the respective impedance element 116 is connected to the other of the pair of transmission wires 112. The impedance elements 116 may be electrically connected in parallel to the pair of transmission wires 112. Impedance elements 116 may be, for example, resistors having a known resistance value and/or complex impedances having complex impedance values. The component including the arrangement of impedance elements 116 between the pair of transmission wires may be according to a ladder, and/or may sometimes be referred to herein as a ladder.

Alternatively or additionally, no impedance elements 116 are used, or regions of the pair of transmission wires 112 do not include impedance elements. In such implementation, the pair of transmission wires 112 alternate between regions that are electrically insulated 118 and regions that are electrically non-insulated 118, effectively creating spaced apart regions of non-insulated wire portions 118. Each non-insulated wire portion 118 effectively acts as an impedance sensor without having an impedance element. The presence of a medium between the transmission wires of the non-insulated wire portion electrically connects the two transmission wires, indicating the presence of the medium by a resulting impedance value of the medium. For example, fluid (e.g., reflux) and/or tissue (e.g., when the two transmission wires both touch the inner wall of the lumen).

As used herein, the term impedance disturbance refers to both possible implementations of impedance elements 116 or electrical connection of wires 112 within electrically non-insulated region 120 such as by fluid (e.g., reflux material) and/or tissue (e.g., inner wall of the esophagus and/or other body cavity).

Impedance elements 116 and/or pairs of non-insulated wire portions 118 may be located at known intervals along catheter 114. Catheter 114 may be implemented as, for example, a probe, a carrier, and/or flexible PCB such as a strip of flexible PCB. The terms probe, carrier, flexible PCB, and catheter may sometimes be interchanged herein. Alternatively, the location of impedance elements 116 and/or pairs of non-insulated wire portions 118 is not known. In such a case, the location may be computed according to an analysis of the delay of the reflected signal, as described herein.

Optionally, the pair of parallel transmission wires 112 are located along a surface of the catheter 114, for example, printed on the surface of a flexible PCB.

Optionally, the pair of parallel transmission wires 112 are embedded within a wall of the catheter 114. A respective recess 122 (e.g., notch, indentation, slot "window") extending within the wall of the catheter 114 is located at a region corresponding to each pair of non-insulated wire portions 120 and/or corresponding to impedance element 116. Both non-insulated wire portions of each pair 112 reside in a respective single common recess 122, and/or each impedance element 116 resides in its own recess 122. The portion of the pair of parallel transmission wires located between recesses are insulated by the wall of the catheter. The recess 122 is sized and/or shaped to accommodate fluid. The fluid filling the recess 122 affects the impedance value of impedance element 116 and/or electrically connects the pair of transmission wires of the respective non-insulated wire portion resulting in a measurable impedance value.

In one example, the transmission wires are embedded in the wall of the polymer feeding tube. In the example, instead of conducting wire pairs, printed conductor pairs incorporating proper isolation layer may be used. As used herein, the term wire may sometimes refer to conductors and/or may include implementations of printed and/or deposited conductor lines (also referred to as conductors), for example as described with reference to *Electrical impedance tomography (EIT): a review. J Med Eng Technol.* 2003; 27:97-108. The polymer wall provides insulation. The sensing ports are located within notches of the polymer wall where the polymer has been removed or injection molded into shape. Exposed (i.e., un-insulated) wires act as electrodes for sensing body fluid and/or contact with tissue according to a measured impedance value. In another example, the transmission wires may be created by deposition of conducting strips on the outer diameter of the tube. The conducting strings are selectively coated with an insulating layer (e.g., biocompatible insulating polymer), and selective left uncoated at other locations corresponding to the impedance elements and/or regions of un-insulated transmission wires.

Alternatively or additionally, the pair of parallel transmission wires 112 are disposed on an outer surface of the catheter 114. The pair of parallel transmission wires 112 are coated with electrically insulating material at spaced apart locations 118. The pair of parallel transmission wires not coated with the electrically insulating material at regions 120 corresponding to the regions of pairs of non-insulated wire portions and/or corresponding to the location of impedance elements 116.

Optionally, the impedance elements 116 and/or pairs of non-insulated parallel transmission wires protrude above the surface of the catheter 114. The protruding impedance elements and/or wires contact the inner wall of the lumen when catheter 114 is located in the lumen, and may be used to monitor, for example, movement and/or location of the catheter 114 within the lumen, for example, forward movement, reverse movement, and/or lateral movement.

Optionally, the catheter 114 is a naso/orogastric tube for being disposed within the esophagus of the patient so that at least a distal end thereof is in the stomach lumen of a patient while at least one segment thereof is in the esophagus. The naso/orogastric tube includes at least one feeding channel for conducting a feeding content within at least one feeding opening located in the distal end. Optionally, the impedance elements and/or regions of the pair of un-insulated portions of the transmission wires are located at the level of the lower esophageal sphincter (LES), and/or above the LES. The location enables monitoring for reflux of stomach contents into the esophagus (e.g., indicative of risk of aspiration) and/or monitoring for displacement of the tube (e.g., into the stomach and/or out of the stomach).

Optionally, computing device 104 is in communication (e.g., via device interface 110) with one or more device controllers 124, for example, a feeding controller, a navigation controller, and a safety controller. Device controllers 124 may be in communication with catheter 114, for example, feeding controller controls automatic feeding of the patient via catheter 114, and navigation controller automatically navigates catheter 14 within the body of the patient. Computing device 104 may generate instructions for manual and/or automatic execution by device controller 124 in response to computed impedance values, for example, when the computed impedance values are indicative of reflux in the esophagus, computing device 104 may generate instructions for execution by the feeding controller for stopping feeding of the patient. In another example, when the computed impedance values are indicative of movement of the catheter, computing device 104 may generate instructions for execution by the navigation controller to adjust the position of the catheter accordingly.

Optionally, computing device 104 is implemented as hardware, for example, circuitry, an assembly of hardware components, an integrated circuit, and/or other architectures. Alternatively or additionally, computing device 104 may be implemented as, for example, a standalone unit, a hardware component, a client terminal, a server, a computing cloud, a mobile device, a desktop computer, a thin client, a Smartphone, a Tablet computer, a laptop computer, a wearable computer, glasses computer, and a watch computer. Computing device 104 may include locally stored software and/or hardware that perform one or more of the acts described with reference to FIG. 2.

Processor(s) 102 of computing device 104 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include one or more processors (homogenous or heterogeneous), which may be arranged for parallel processing, as clusters and/or as one or more multi core processing units.

As used herein, the term processor may sometimes be interchanged with the term computing device.

Storage device (also known herein as a program store, e.g., a memory) 106 stores code instructions implementable by processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Storage device 106 stores code instruction 106A that execute one or more acts of the method described with reference to FIG. 2. Alternatively or additionally, one or more acts of the method described with reference to FIG. 2 are implemented in hardware.

Computing device 104 may include a data repository 126 for storing data, for example, a dataset that stores a history of computed impedance values and/or associated times. Data repository 126 may be implemented as, for example, a memory, a local hard-drive, a removable storage unit, an optical disk, a storage device, and/or as a remote server and/or computing cloud (e.g., accessed via a network connection).

Computing device 104 includes and/or is in communication with a user interface 128 that includes a mechanism for a user to enter data (e.g., patient information, set baseline) and/or view presented data (e.g., impedance values for each impedance element and/or each pair of un-insulated transmission wires, detected changes in impedance values). Exemplary user interfaces 128 include, for example, one or more of, a touchscreen, a display, a keyboard, a mouse, and voice activated software using speakers and microphone. External devices communicating with computing device 104 may be used as user interfaces 128, for example, a smartphone running an application may establish communication (e.g., cellular, network, short range wireless) with computing device 104 using a communication interface (e.g., network interface, cellular interface, short range wireless network interface).

Computing device 104 includes device interface 110 that provides electrical communication with one or more device controllers 124. Device interface 110 may be implemented as, for example, a network interface card, a hardware interface card, a wireless interface, a physical interface for connecting to a cable, a virtual interface implemented in software, communication software providing higher layers of connectivity (e.g., application programming interface (API), software development kit (SDK), and/or other implementations.

At 202, a catheter is selected. As described herein, different catheters are available, including catheters with one or multiple pairs of transmission lines located around the outer circumference of the catheter, catheters with impedance elements or without impedance element but instead having regions of non-insulated portions of the pairs of transmission wires, catheters with a recess for capturing fluid at locations corresponding to the impedance elements and/or regions of non-insulated portions of the transmission wires, catheters with protruding impedance elements and/or regions of non-insulated portions of the transmission wires. The catheters may be for different parts of the body, for example, feeding tube for insertion into the esophagus, endotracheal tube for insertion into the trachea, urinary tube for insertion into the bladder, and vascular tube for insertion into the blood vessels and/or heart.

The configuration of the catheter may be selected according to the target application, for example, monitoring for movement of the catheter and/or monitoring for the presence of fluid within the body cavity where the catheter is located.

At 204, the selected catheter is inserted into the cavity of the body of the patient. The catheter may be connected to the transceiver, to the computing device, and/or to the device controller.

Figure 3:
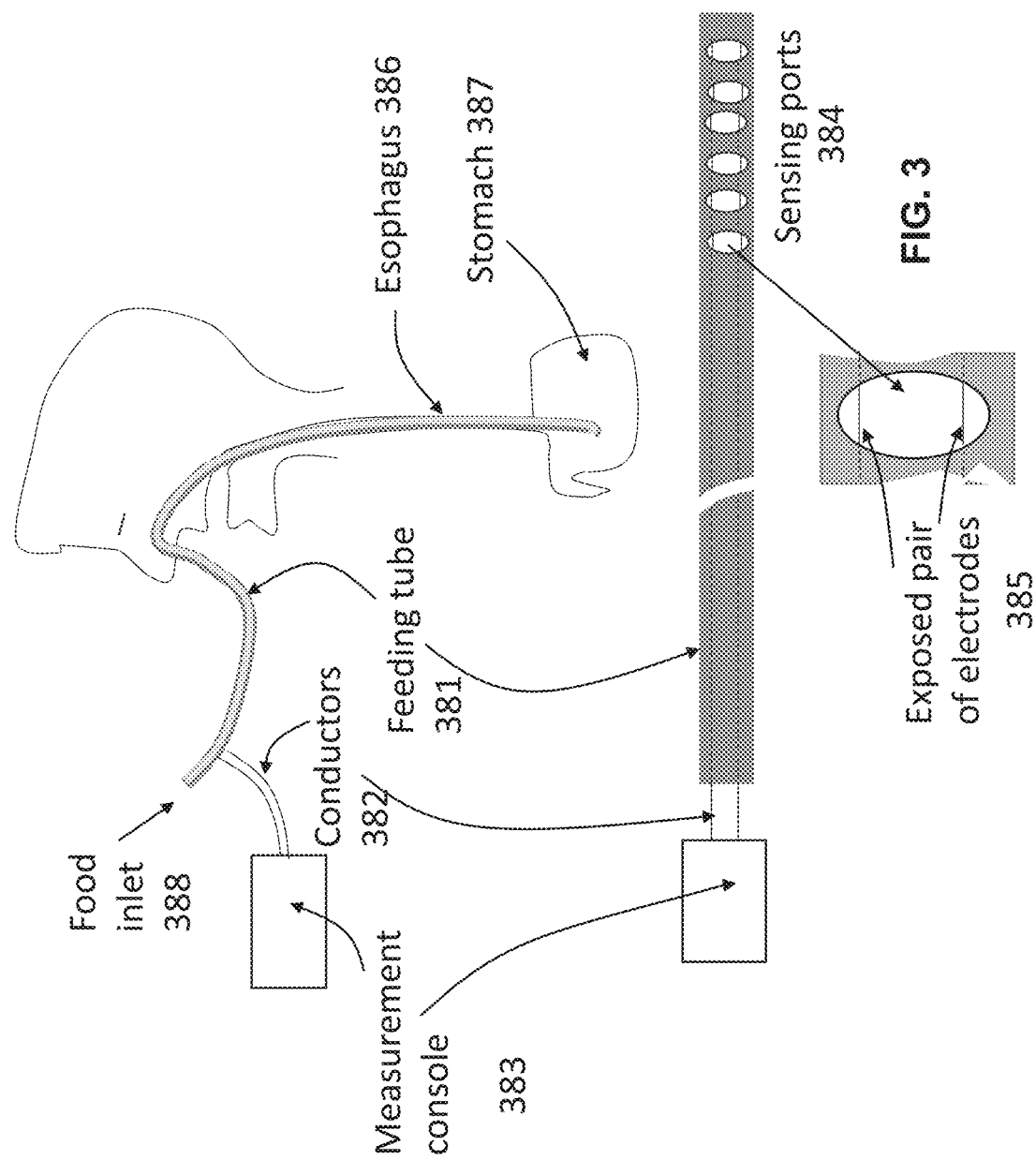
FIG. 3 is a schematic depicting an exemplary implementation of the catheter as a feeding tube for enteral feeding of the patient, in accordance with some embodiments of the present invention.

Reference is now made to FIG. 3, which is a schematic depicting an exemplary implementation of the catheter as a feeding tube for enteral feeding of the patient, in accordance with some embodiments of the present invention. A feeding tube 381 includes a pair of transmission wires and multiple spaced apart impedance sensing ports 384, optionally at a location on the feeding tube corresponding to the level of the LES, below the LES, and/or above the LES at the lower portion of the esophagus. Each impedance sensing port 384 includes a region of the pair of transmission wires 385 that are un-insulated. The pair of transmission wires located between sensing ports 384 are insulated. In one example, the transmission wires are embedded in the wall of the polymer feeding tube. The polymer wall provides insulation. The sensing ports are located within notches of the polymer wall where the polymer has been removed or injection molded into shape. Exposed (i.e., uninsulated) wires 385 act as electrodes for sensing body fluid and/or contact with tissue according to a measured impedance value. It is noted that alternatively or additionally, sensing elements may be located at each sensing port. The sensing elements and/or uninsulated wires may be located within a recess and/or may protrude above the surface of the feeding tube. The pair of transmission wires may be connected to a measurement console 383 (e.g., transceiver) located outside the body of the patient, optionally via a conductor 382. Feeding tube 381 includes a food inlet 388 for delivery of food into a stomach 387 of the patient when feeding tube 381 is located within the esophagus 386.

At 206, an electrical signal is created and transmitted (also referred to herein as injected) into the pair of parallel transmission wires, optionally into the proximal end of the pair of parallel transmission wires located outside the body of the patient. The electrical signal may be created and transmitted by the transmitter component and/or by the transceiver. The computing device may generate instructions for controlling the transmission of the electrical signal by the transmitter.

Optionally, the electrical signal is a pulse. Optionally, a single electrical pulse is injected. Multiple pulses may be injected, were each pulse is injected after a sequence of reflected pulses is received. Each pulse may have a pre-defined pulse width (e.g., denoted Tw). Pulses may be spaced apart in time, for example, an interval of time denoted as T. Time intervals between pulses may be equal, or variable. Multiple pulses time spaced pulses may be injected.

Alternatively, the injected electrical signal is continuous (i.e., for a defined time interval), optionally a wave, optionally a harmonic wave for example, a sinusoidal wave. Multiple harmonic waves may be injected, each at a respective frequency. Each wave at each frequency may be injected after the reflections from the previous wave at the previous frequency are received.

The characteristic impedance of the pair of parallel transmission wires is denoted herein as $Z_0$.

The electrical signal (e.g., pulse, wave) propagates at a speed which may be computed (depending on the electrical properties of the transmission wires) along the transmission wires until meeting a disturbance (also known as impedance mismatch or discontinuity) is met, such as the impedance elements and/or connection between un-insulated portions of the transmissions wires (e.g., due to body fluid and/or tissue forming an electrical connection between the pair of un-insulated portions of the transmission wires). A portion of the injected signal is reflected and returns to the source (e.g., transceiver), and another portion of the injected signal continues to travel to the next disturbance.

It may be assumed that a small portion of the applied signal is reflected, that most of the applied signal continues to the next disturbance, and that most of the reflections eventually arrive back to the receiver (e.g., transceiver).

Optionally, the pair of parallel transmission wires are terminated (e.g., at the distal end portion of the catheter) with an impedance element having a value about equal to the value of the characteristic impedance. The terminal impedance element absorbs any leftover signal at the end of the line.

At 208, the reflections from the multiple impedance elements, and/or from the multiple pairs of non-insulated portions of the transmission wires are received, optionally by a receiver and/or transceiver. The reflections are optionally received at the same proximal end where the signals are injected, located outside the body of the patient. The received reflections may be directed into the computing device for further processing, as described herein, and/or directed into other components (e.g., A/D converter) for further processing, as described herein.

Optionally, when a pulse is injected, multiple reflections are received. The reflected signals are spaced apart in time. A single reflection from each impedance disturbance (it is noted that additional reflections occurring in the reverse direction may be ignored for simplicity and/or lack of significance) is received. Reflections from relatively more proximal impedance disturbances are received with a smaller delay (e.g., relative to the time of the injected pulse) than reflections from relatively more distance impedance disturbances.

One or more of the received reflections may be selected, for example, by a timing gate, according to the estimated expected time of arrival of the received reflections. It is noted that in some cased the location of the impedance windows is a priori known by its design and hence using the time gating technique the noise is reduced.

Irrelevant reflections, for example, reflection occurring alone the transmission line due to errors and/or dirt, and/or signals that get reflected multiple times between disturbance elements before returning and being measured, and/or attenuated signals, may be ignored by the timing. Reflected signals having a delay return time corresponding to the location of known impedance disturbances may be retained (i.e., a single round trip), while other signals having other delay times that do not directly correspond to the round trip delay of a certain impedance disturbance (e.g., due to repeated reflections, i.e., bouncing back and forth between impedance disturbances) may be filtered out and/or otherwise ignored.

Figure 4:
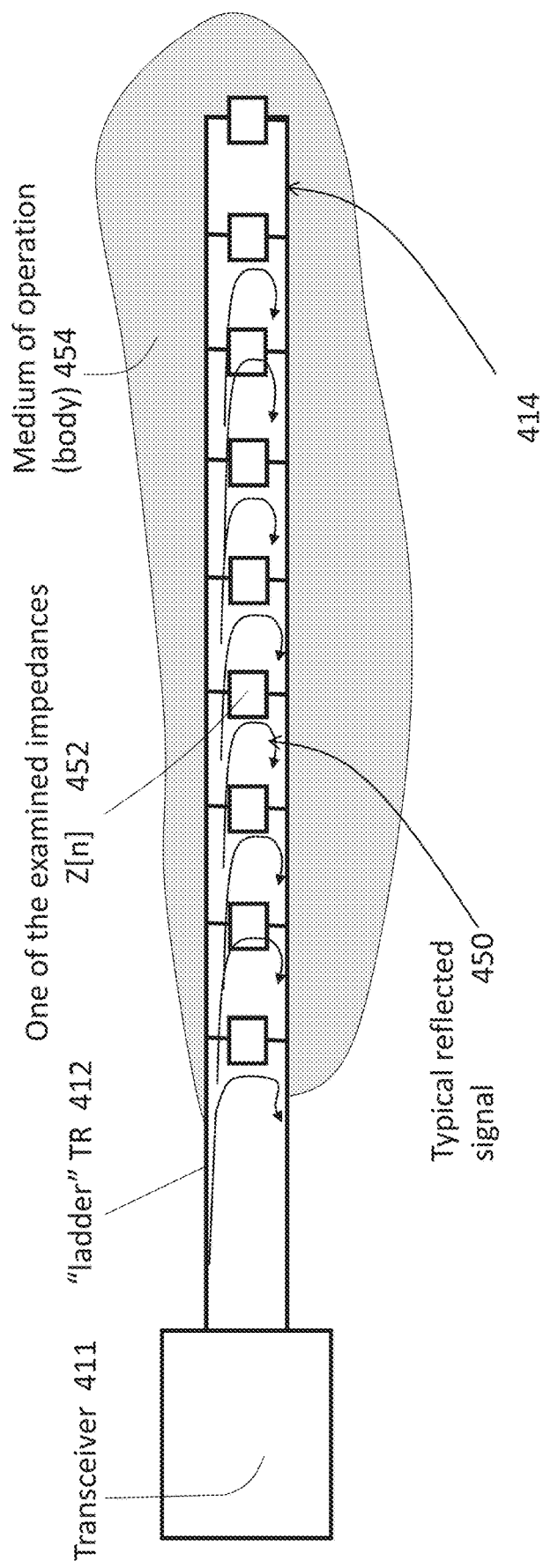
FIG. 4 is a schematic depicting reflections from multiple impedance elements of a signal (e.g., current) injected by a transceiver into a transmission line, in accordance with some embodiments of the present invention.

Reference is now made to FIG. 4, which is a schematic depicting reflections 450 from multiple impedance elements (e.g., one shown as 452) of a signal injected by a transceiver 411 into a transmission line 412, in accordance with some embodiments of the present invention. Transmission lines 412 are located on a catheter 414 located within a body of a patient 454, optionally within a cavity, for example, the esophagus.

Figure 5:
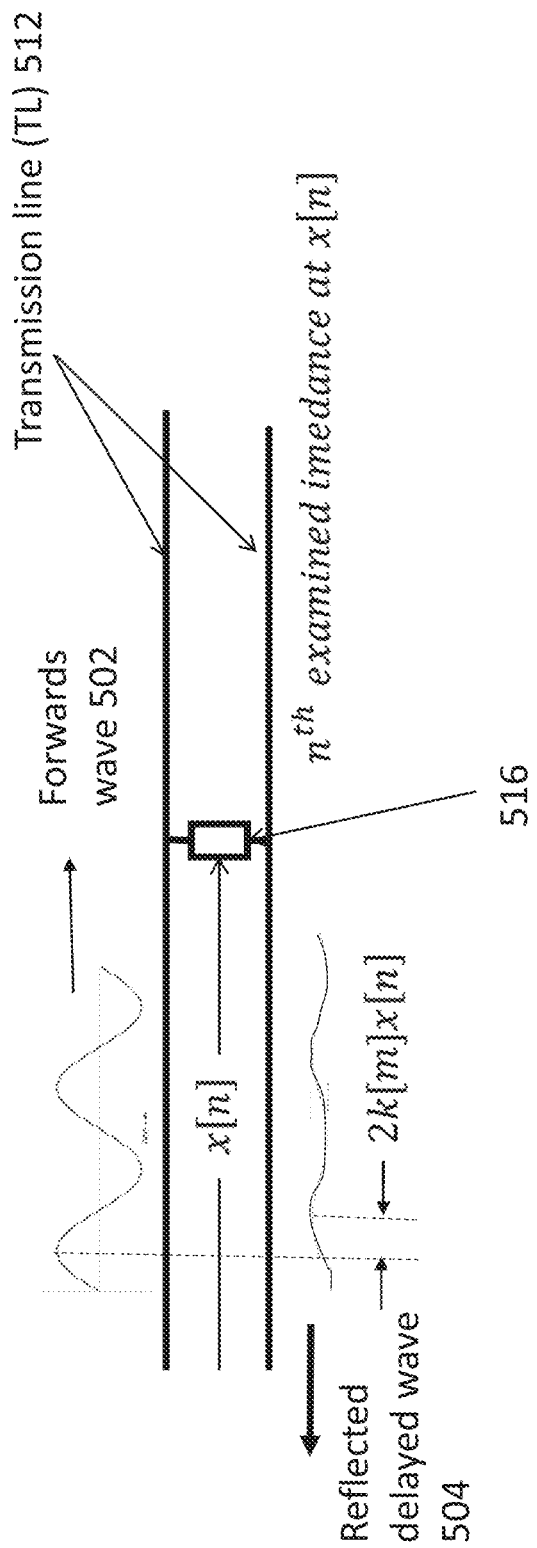
FIG. 5 is a schematic depicting an injected harmonic signal and example of a reflection of the injected signal off an impedance element located between a pair of transmission wires, in accordance with some embodiments of the present invention.

Reference is now made to FIG. 5, which is a schematic depicting an injected harmonic signal 502 and example of a reflection of the injected signal 504 off an impedance element 516 located between a pair of transmission wires 512, in accordance with some embodiments of the present invention.

Referring now back to FIG. 2, at 210, the reflections of the electrical signal from each of the impedance elements are measured and/or analyzed to compute an impedance value for each respective impedance element and/or each respective pair of non-insulated wire portions. The measurement and/or analysis may be performed, for example, by the transmitter, transceiver, computing device, and/or other components described herein (e.g., A/D converter, gate, integrator, mixer).

Processing is according to whether the injected signal is a harmonic signal, or whether the injected signal is a pulse.

When the injected signal is a harmonic signal, optionally, the multiple reflections are mixed (e.g., multiplied) with a reference harmonic signal selected to eliminate or significantly reduce the radiofrequency (RF) component to identify the intermediate frequency (IF) component which is a function of one of the measured impedance values corresponding to a selected impedance element. Each reference harmonic signal is selected from a plurality of harmonic signals, each having a different frequency. The number of reference harmonic signals may be equal to the number of impedance elements. The inversion of the IF component is computed to compute the impedance value corresponding to the selected impedance element. The mixing of the reflections with the reference harmonic signal is iterated for each reference harmonic signal corresponding to each of the impedance elements, for computing the impedance value corresponding to each respective impedance element. In this manner, the impedance value measured by each impedance element is extracted from the multiple received reflections of the injected signal. The impedance element(s) (e.g., the selected impedance element) may be identified according to an analysis of a phase shift of the reflections relative to the electrical signals. The phase shift may be calculated as a function of a location of the selected impedance element.

The impedance value of each impedance element and/or the impedance value of the medium electrically connecting pairs of un-insulated portions of the electrical transmission wires (e.g., reflux, body fluid, tissue) may be computed by computing the spectral response (e.g., DFT) of the impedance elements to the injected electrical signal, and performing an inverse transform of the spectral response.

The process may be iterated for multiple waves, each at a different frequency may be injected, optionally sequentially. The results of the analysis from the different frequencies may be used to improve the accuracy of the measurement of the impedance values.

When the injected electrical signal is continuous, optionally a harmonic wave such as a sinusoidal wave, the phase and/or amplitude of the reflected wave are changed in comparison to the injected wave. The change in phase and/or amplitude is according to the disturbance impedances (e.g., impedance elements and/or electrical connections between pairs of non-insulated portions of the transmission wires (e.g., by body fluid and/or tissue) according to the following relationship:

$$r[i] = \frac{Z_i - Z_0}{Z_i + Z_0}$$

where:

$Z_0$ denotes the characteristic impedance of the pair of transmission wires, $$Zi = Ri + j\,Xi$$

r[i] denotes the reflected signal reflected from impedance disturbance Zi.

Figure 6:
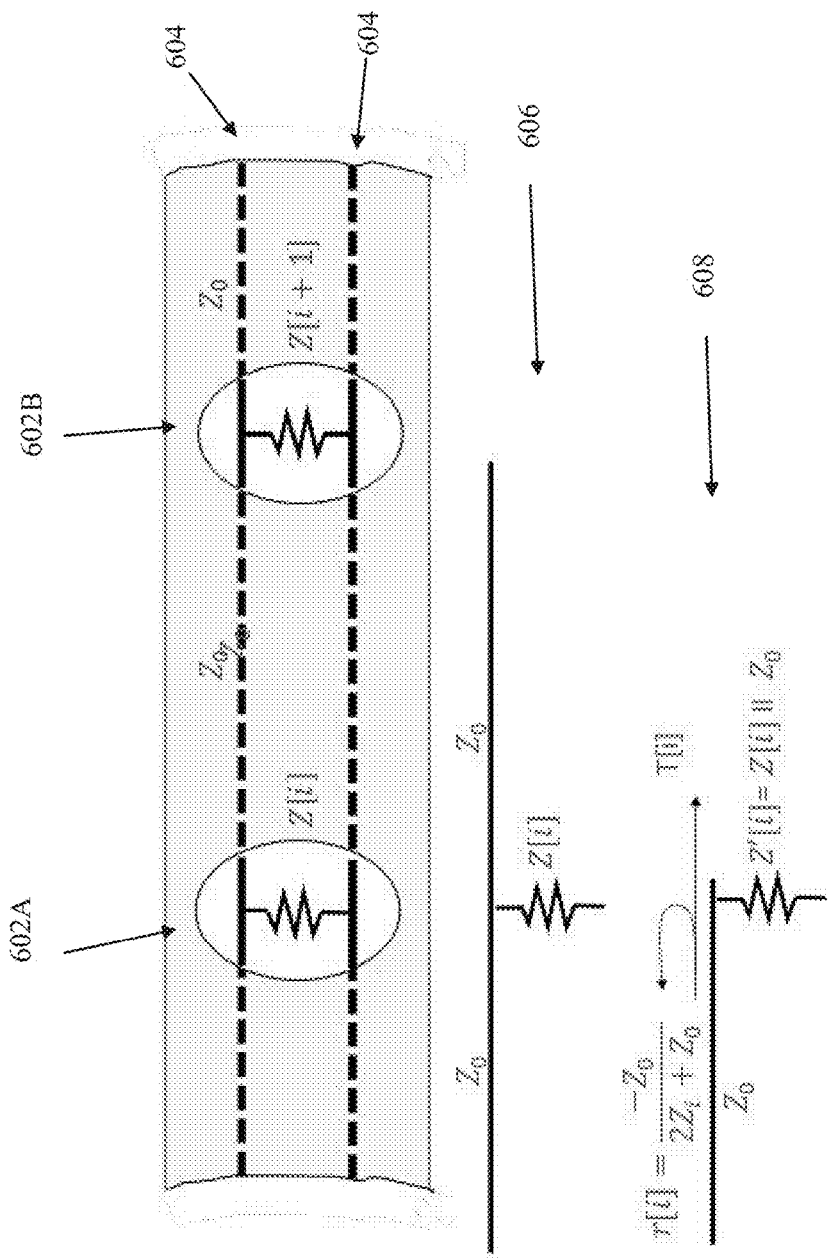
FIG. 6 is a schematic depicting two impedance elements, to help understand computation of the reflected signals, in accordance with some embodiments of the present invention.

Reference is now made to FIG. 6, which is a schematic depicting two impedance elements 602A-B (or two uninsulated portions of a pair of parallel transmission wires 604 that are electrically connected, for example, by the presence of fluid and/or tissue), to help understand computation of the reflected signals, in accordance with some embodiments of the present invention. Impedance element 602A (or pair of electrically connected un-insulated wires) has impedance value Z[i], and impedance element 602B (or pair of electrically connected un-insulated wires) has impedance value Z[i+1]

A more accurate calculation may be performed by viewing the reflecting impedance as composed of Zi and Zo (as shown by arrow 606) in parallel, i.e. $Z_i' = Z_i \| Z_0$ (as shown by arrow 608), where r[i] denotes the reflected wave from impedance element (or electrically connected pair of non-insulated portions of the transmission wires) Zi:

$$r[i] = \frac{-Z_0}{2Z_i + Z_0}$$

All are complex values in the general case.

Referring now back to FIG. 2, when the input wave form is:

$$e^{-j\omega[m]t}$$

where ω[m] denotes the frequency of the injected signal

The reflected wave from the $n^{th}$ disturbance impedance may be computed according to the following (neglecting the additional phase change):

$$r[n,m]e^{-j(\omega[m]t - k[m] \times [n])}$$

The total reflected signal at frequency ω[m] from all N disturbance impedances may be represented and/or computed according to the following:

$$S'[m] = \Sigma_{n=0}^{n=N-1} r[n,m] e^{-j(\omega[m]t - k[m] \times [n])}$$

which when mixed (i.e., multiplied) by the complementary signal reference (also referred to herein as the reference harmonic signal) denoted:

$$e^{+j\omega[m]t}$$

demodulates the signal to yield the following representation:

$$S[m] = \Sigma_{n=0}^{n=N-1} r[n,m] e^{-j(k[m] \times [n])}$$

where S denotes the Discrete Fourier Transform (DFT) of r, hence the reconstruction of r is based on the inversion of S, and computed according to the following mathematical relationship:

$$r[n] = IDFT\{S[m]\}$$

The following represents a mathematical proof of the above described process for extracting the reflected signal from each one of the impedance elements.

When frequencies and the distance between the elements are all equally spaced (N units):

$$IDFT\{S[m]\} = \sum_{m=0}^{m=N-1} S(m) e^{+j\frac{2\pi}{N}mu}$$

Reversing the summation order:

$$= \sum_{n=0}^{n=N-1} r(n) \underbrace{\sum_{m=0}^{m=N-1} e^{-j\frac{2\pi}{N}(n-u)m}}_{\delta(n-u)} = \sum_{n=0}^{n=N-1} r(n)\delta(n-u) = r(u)$$

QED

Which yield the desired result:

$$Z[i] = \frac{1 + r[i]}{1 - r[i]}$$

Optionally, when the injected signal is a pulse, or multiple pulses spaced apart in time, the sequence of reflected pulses are received. One or more reflected pulses corresponding to a reflection from a certain impedance disturbance are selected, for example by a timing gate. The selected pulse may be integrated, optionally converted into digital format from analogue format, and fed as input for computing the impedance value of the impedance disturbance from which the selected pulse is reflected from. The following equation may be used to compute the impedance value (denoted Z) of a certain impedance disturbance (denoted i) denoted Z[i] according to the selected reflected signal reflected from the certain disturbance, denoted r[i]:

$$Z[i] = \frac{1 + r[i]}{1 - r[i]}$$

It is noted that the reflected signal may be computed according to a voltage value (denoted Vi).

Figure 7:
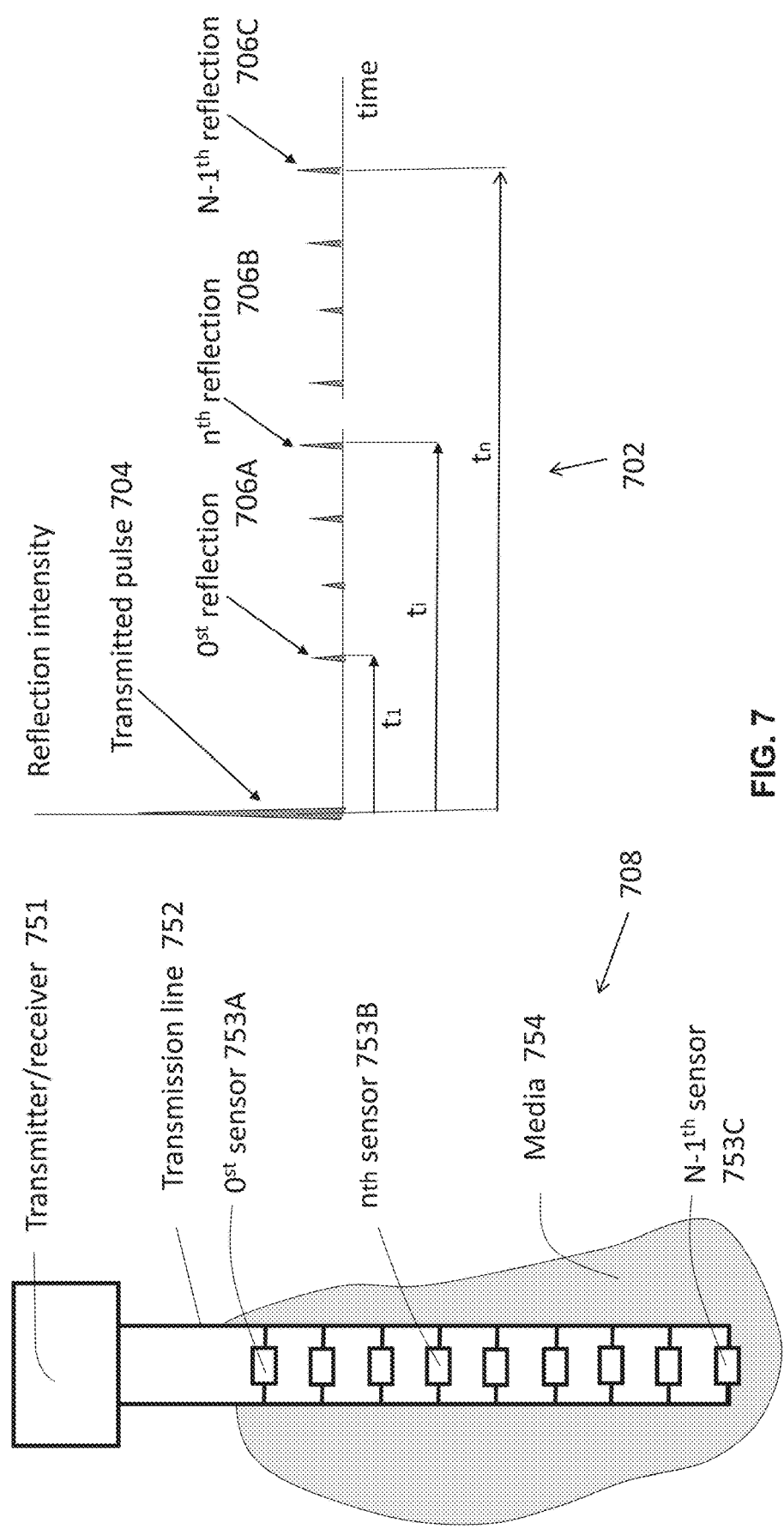
FIG. 7 is a graph of signal intensity as a function of time, depicting a transmitted pulse at time zero, and multiple reflections of the transmitted pulse from impedance elements 0, n, and N−1, at respective times $t_1$, $t_i$, and $t_n$, in accordance with some embodiments of the present invention.

Reference is now made to FIG. 7, which includes a graph 702 of signal intensity as a function of time, depicting a transmitted pulse 704 at time zero, and multiple reflections of the transmitted pulse 706A-C from impedance elements 0, n, and N−1, at respective times $t_1$, $t_i$, and $t_n$, in accordance with some embodiments of the present invention. Schematic 708 depicts impedance elements 753A-C corresponding to reflections 706A-C of graph 702. Impedance elements 753A-C are connected to a pair of transmission wires (also referred to herein as transmission lines) 752 optionally in a media 754, as described herein, which are connected to a transmitter/receiver 751, as described herein.

Figure 8:
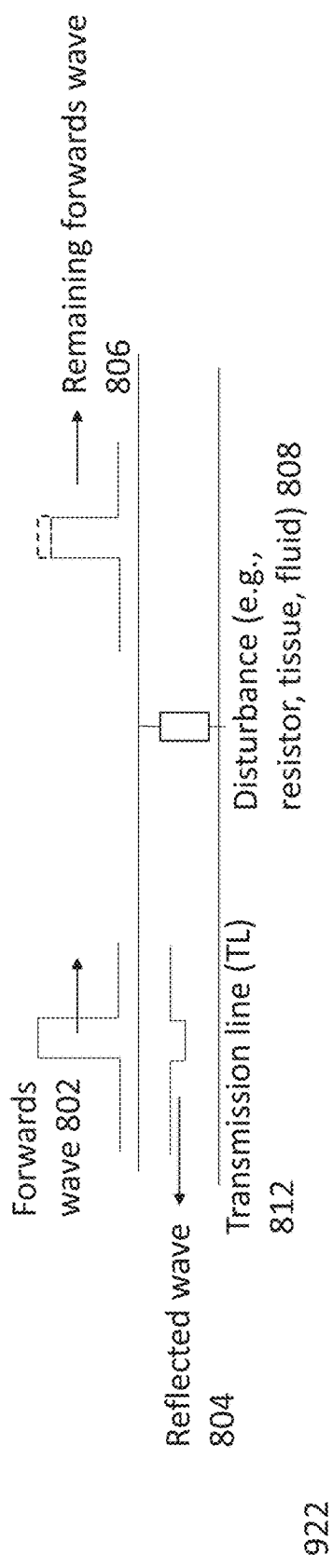
FIG. 8 is a schematic depicting an injected electrical pulse signal, a reflection of the injected pulse, and a remaining component of injected pulse in response to an impedance disturbance of a transmission line, in accordance with some embodiments of the present invention.

Reference is now made to FIG. 8, which is a schematic depicting an injected electrical pulse signal 802, a reflection 804 of the injected pulse 804, and a remaining component 806 of injected pulse 802 in response to an impedance disturbance 808 (e.g., impedance element, fluid and/or tissue) of a transmission line 812, in accordance with some embodiments of the present invention.

Figure 9:
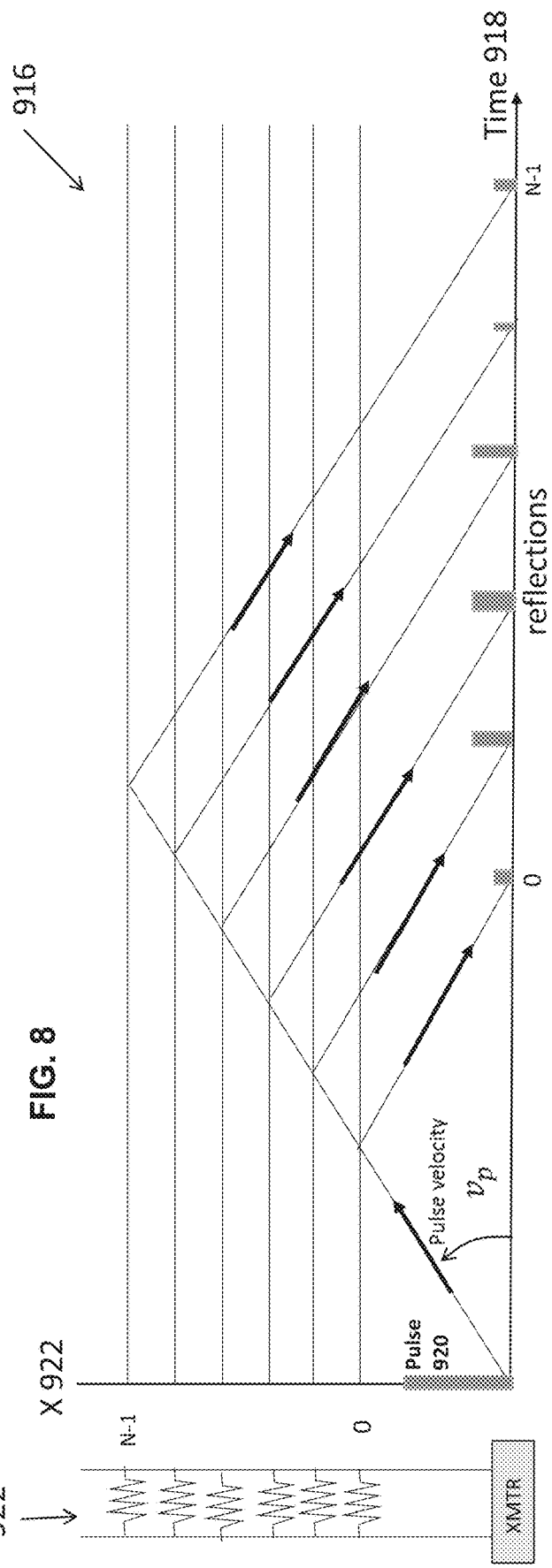
FIG. 9 is a R-T range-time (R-T) diagram, conceptually depicting reflections along a time axis of an injected pulse, off multiple impedance disturbances depicted along a distance axis, in accordance with some embodiments of the present invention.

Reference is now made to FIG. 9, which is a range-time (R-T) diagram 914, conceptually depicting reflections along a time axis 918 (on the x-axis), of an injected pulse 920, off multiple impedance disturbances (denoted 0 to N−1) depicted along a distance axis 922 (on the y-axis), in accordance with some embodiments of the present invention. The location of the impedance disturbances along the pair of transmission wires corresponding to the R-T diagraph is shown in a schematic 916.

Figure 10:
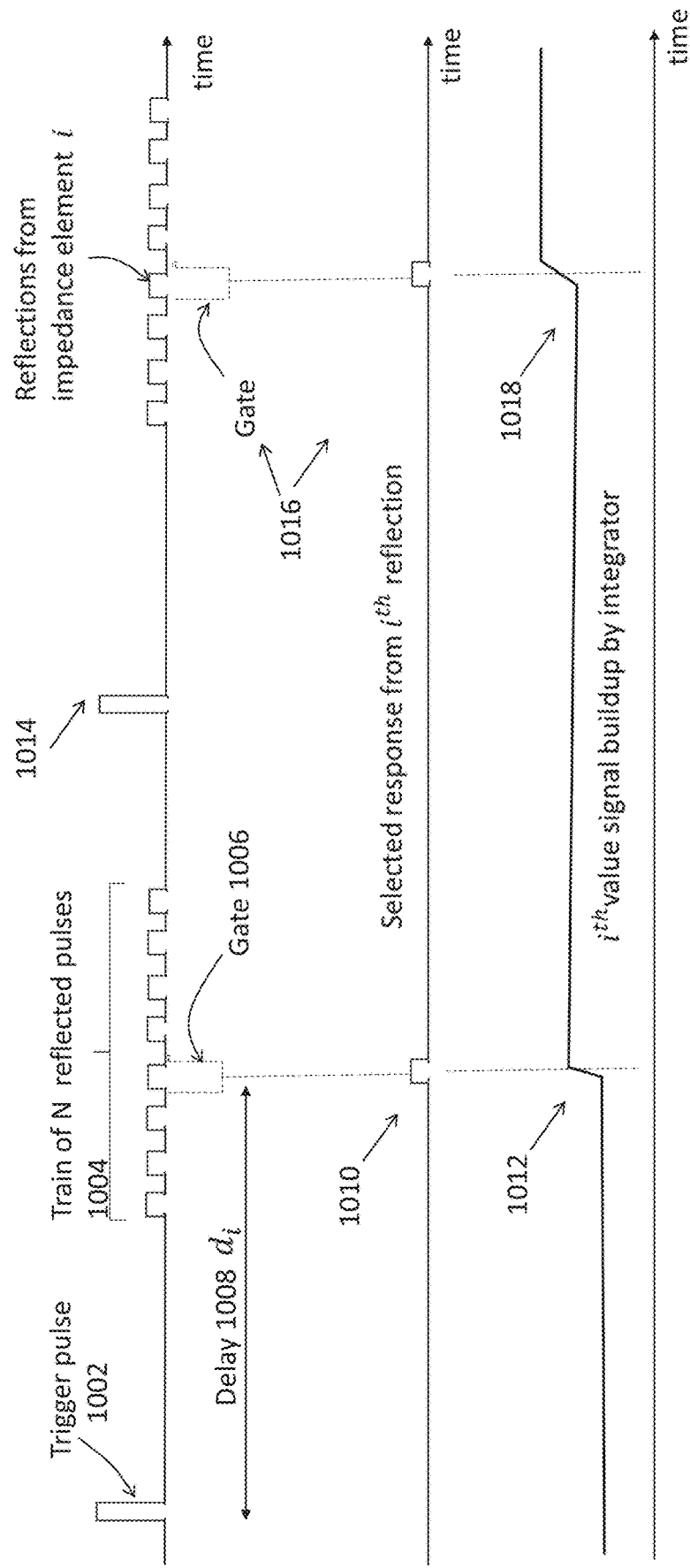
FIG. 10 is a schematic graphically depicting the process of computing impedance value for a certain impedance disturbance based on an injected pulse, in accordance with some embodiments of the present invention.

Reference is now made to FIG. 10, which is a schematic graphically depicting the process of computing impedance value for a certain impedance disturbance based on an injected pulse (also referred to herein a probing pulse, or a trigger pulse), in accordance with some embodiments of the present invention. A trigger pulse 1002 is injected into the pair of transmission wires. A sequence (e.g., train) of reflected pulses 1004 is received, where each reflection is from one of multiple impedance disturbances. A gate 1006 may select one of the reflections 1004 corresponding to a certain impedance disturbance according to a estimated delay (denoted di) 1008 from the time of injection of the trigger pulse according to the location of the certain impedance disturbance along the transmission wires (e.g., compute estimated time for the signal to travel from the transceiver to the certain impedance disturbance along the transmission wires and back to the transceiver). The selected reflected signal 1010 is selected from the rest of the received signals, for example, by a filter. An integrator may integrate reflected signal 1012. Optionally, the process is iterated, by transmission of another pulse to obtain another sequence of pulses (arrow 1014). The gate selects another reflection corresponding to the same impedance disturbance (arrow 1016). The integrator adds 1018 the selected reflections to the previous reflection, to buildup a value of the signal corresponding to the certain impedance disturbance. The impedance value is computed according to the integrated value from the multiple integrations of the isolated reflected signal.

At 212, an impedance value baseline may be established for each of the impedance elements and/or pairs of non-insulated wire portions, for example, by the computing device. Alternatively, no impedance value is established. The absolute value of each impedance may be provided, and/or the impedance values may be normalized relative to each other.

The impedance value baseline may be established, for example, manually set by a user (e.g., by making a selection via a user interface, for example, pressing a baseline set icon), automatically set by code (e.g., when a set of rules is met, for example, all impedance disturbances have impedance values indicating no reflux is present in the esophagus), and/or automatically set according to the initial set of readings. The baseline may be repeatedly reset, for example, to monitor progress of a patient. The baseline may be manually set, for example, after the user performs a clinical evaluation to determine that the patient is at a desired baseline, for example, making sure there is no current reflux present in the esophagus of the patient and/or evaluating an x-ray to make sure that the feeding tube is located in the correct position.

At 214, instructions may be generated by the computing device in response to the detected change in impedance values and/or in response to absolute measurement in impedance values (e.g., when no baseline is used) according to a requirement (e.g., threshold, range). Instructions may be generated, for example, according to a set of rules, selected from predefined instructions according to impedance values and/or changes in impedance values, and/or generated by trained machine learning code. The instructions may be for execution by one or more other device controllers. The generated instructions may be automatic instructions (e.g., code, script) for execution by a processor(s) of the device controllers. The generated instructions may be for manual execution by a user, for example, text, images and/or video presented on a display for a user to follow, and/or audio instructions played over speakers.

Exemplary instructions include: when the computed impedance values are indicative of reflux in the esophagus, the instructions are for execution by a feeding controller for stopping feeding of the patient via the catheter. In another example, when the computed impedance values are indicative of movement of the catheter, the instructions are for execution by a navigation controller for adjustment of the position of the catheter accordingly, for example, to correct the displacement of the catheter and/or to move the catheter to a new location.

At 216, data is provided, for example, presented on a display, stored in a memory, forwarded to a remote server, and/or provided to another process for further processing. Optionally, the data is displayed on a display, optionally within a graphical user interface (GUI) presented on the display.

Optionally, the real time impedance values measured for each impedance element and/or each pair of un-insulated region of the transmission wires is presented on the display, for example, as a bar graph. The real time changes in impedance values relative to baseline may be computed and presented for each impedance element and/or each pair of un-insulated region of the transmission wires.

An indication of the generated instructions may be presented, and/or the generated instructions themselves may be presented for manual implementation.

Optionally, the identified intermediate frequency is rectified, digitized, and presented on the display, optionally within the GUI.

At 218, one or more features described with reference to acts 206-216 are iterated for monitoring for statistically significant changes, optionally relative to each impedance baseline. Instructions may be dynamically computed according to the real time measured impedance values, and/or the real-time measured impedance values may be dynamically presented on the display.

The iterations represent a monitoring of the impedance values. Changes to the impedance values are indicative of a change in the medium contacting the respective impedance element and/or pair of un-insulated transmission wires, denoting, for example, the presence of fluid (e.g., reflux in the esophagus) and/or displacement of the catheter (e.g., forward, reverse, lateral).

Optionally, the impedance values are converted into other measurements, for example, pressure, temperature, biochemical composition and/or pH. The converted values may be established as baseline and monitored for changes thereof.

Figure 11:
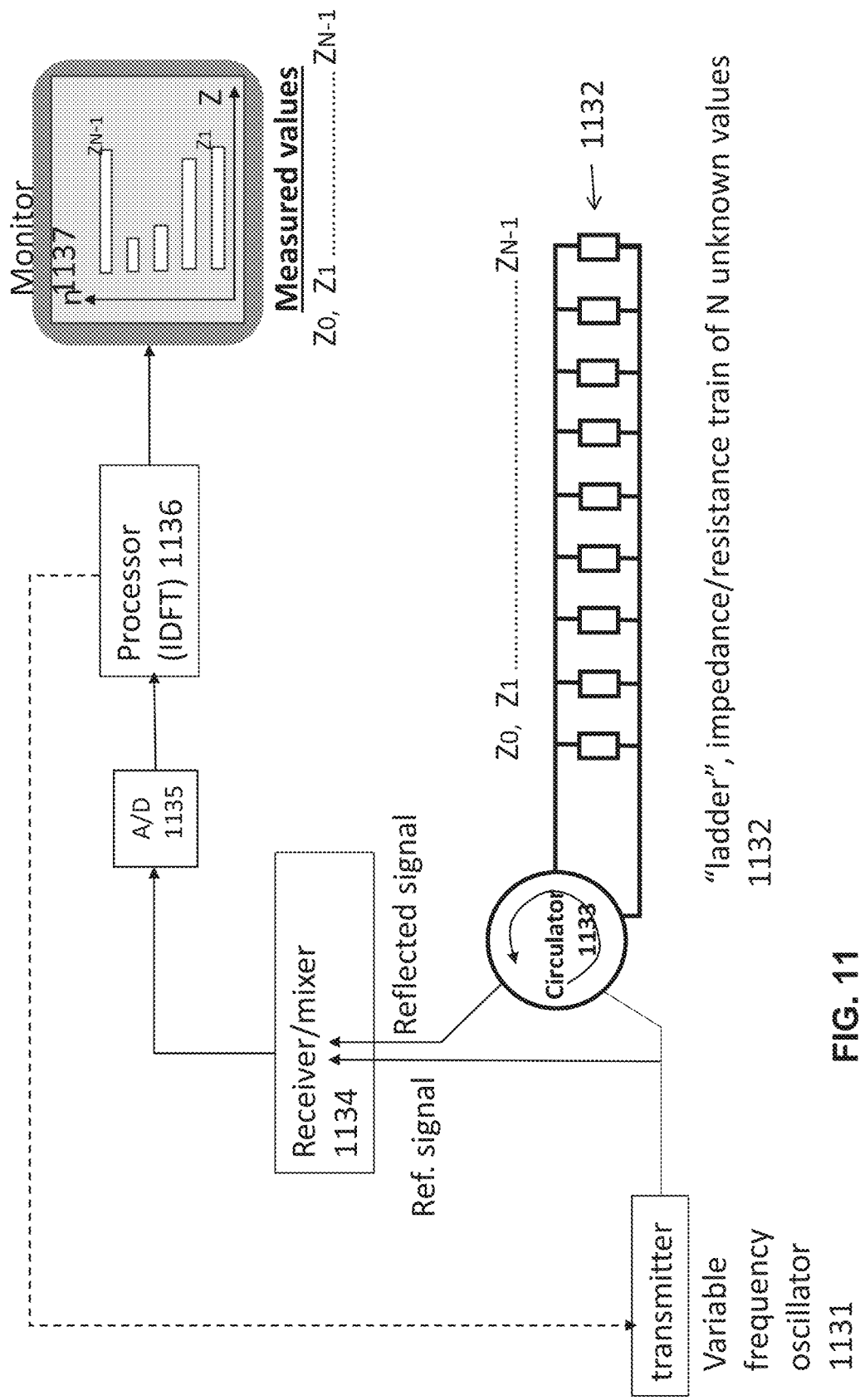
FIG. 11 is a schematic of an exemplary implementation of a system for measuring multiple impedance values designed for operation in harmonic mode, in accordance with some embodiments of the present invention.

Reference is now made to FIG. 11, which is a schematic of an exemplary implementation of a system for measuring multiple impedance values designed for operation in harmonic mode using a harmonic injected signal (e.g., computations performed in the frequency domain), in accordance with some embodiments of the present invention. An apparatus 1150 including two transmission lines having multiple spaced apart connected (e.g., in parallel) impedance disturbances 1132 (denoted $Z_0, Z_1 \ldots Z_{N-1}$) having unknown impedance values, as described herein, is provided. Additional optionally exemplary components connected to apparatus 1150 include:

A variable frequency, tunable source oscillator (i.e., transmitter component) 1131, which may generate waves having a frequency selected from the range of, for example, 80 to 120 megahertz (MHz).

A circulator 1133 that directs output (i.e., generated probing signal) of oscillator and/or transmitter 1131 into apparatus 1150, and directs output (i.e., reflections of the injected probing signal) of apparatus 1150 into a receiver and/or mixer component 1134.

A receiver and/or mixer 1134 that receives the reference signal (i.e., the injected signal) from transmitter 1131, and the reflected signal, and/or mixes the reflected signal with a reference signal for demodulating the desired signal, as described herein.

An analogue to digital (A/D) component 1135 that converts the demodulated analog signal into a sequence (also referred to herein as a train) of digital signals.

A hardware processor 1136 that receives the sequence of digital signals and computes the Inverse Discrete Fourier Transform (IDFT) for computing the impedance values for each of the impedance elements $Z_0, Z_1 \ldots Z_{N-1}$.

A monitor 1137 that displays the impedance values computed for each one of the impedance elements $Z_0, Z_1 \ldots Z_{N-1}$, for example, as numerical values and/or as a bar graph.

Figure 12:
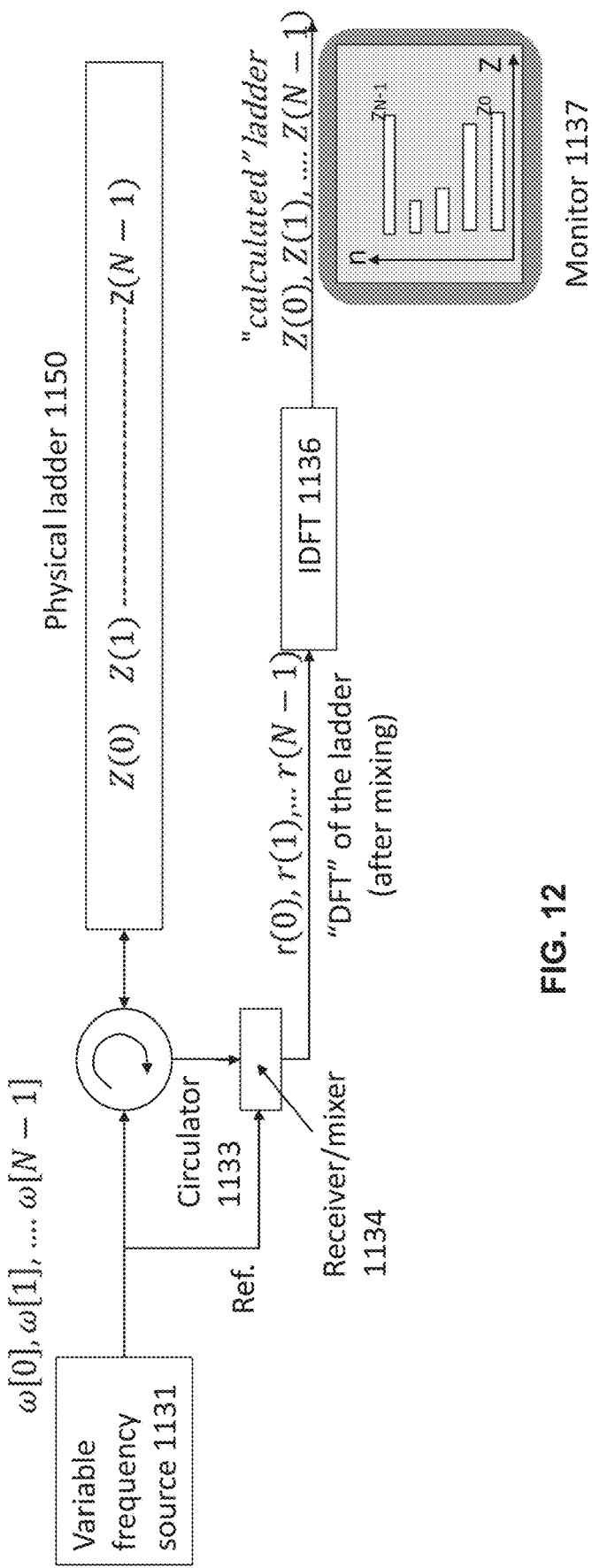
FIG. 12 is a schematic corresponding to FIG. 11, denoting mathematic representations of computed signals, in accordance with some embodiments of the present invention.

Reference is now made to FIG. 12, which is a schematic corresponding to FIG. 11, denoting mathematic representations of computed signals, in accordance with some embodiments of the present invention. Apparatus 1150 includes impedance elements denoted $Z_0, Z_1 \ldots Z_{N-1}$ having respective impedance values denoted $Z(0), Z(1), \ldots Z(N-1)$. Variable frequency source 1131 generates multiple signals for injection into apparatus 1150, each one at a different frequency, denoted as $\omega[0], \omega[1], \ldots \omega[N-1]$. Receiver/mixer 1134 receives the reflections of the injected signals, and mixes the reflected signals with the injected signals (acting as the reference signals) to output demodulated desired signals $r(0), r(1), \ldots r(N-1)$. Processor 1136 receives the digital signals, computes the IDFT, and outputs impedance values $(0), Z(1), \ldots Z(N-1)$ for each of the impedance elements $Z_0, Z_1 \ldots Z_{N-1}$, which may be displayed on monitor 1137.

Figure 13:
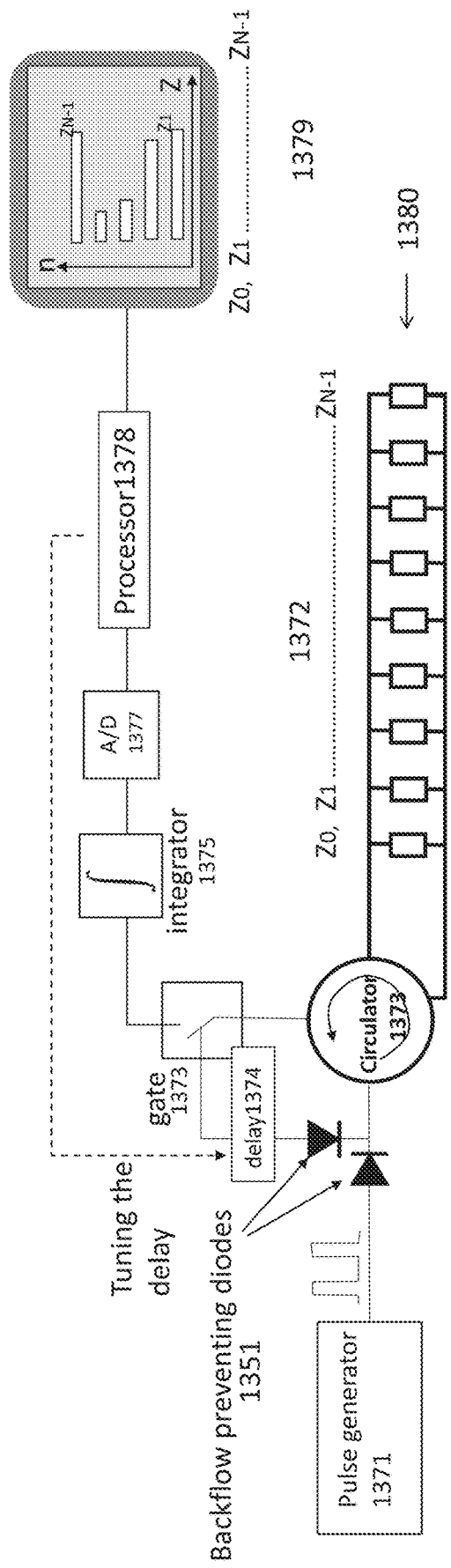
FIG. 13 is a schematic of an exemplary implementation of a system for measuring multiple impedance values designed for operation based on an injected pulse signal, in accordance with some embodiments of the present invention.

Reference is now made to FIG. 13, which is a schematic of an exemplary implementation of a system for measuring multiple impedance values designed for operation based on an injected pulse signal (also referred to as an injected pulse, trigger pulse, probe pulse), in accordance with some embodiments of the present invention. An apparatus 1372 including two transmission lines having multiple spaced apart connected (e.g., in parallel) impedance disturbances 1380 (denoted $Z_0, Z_1 \ldots Z_{N-1}$) having unknown impedance values, as described herein, is provided. Additional optionally exemplary components connected to apparatus 1372 include:

A pulse generating 1371 that generates pulses. The pulse shape and/or pulse width and/or time delay between pulses may be selected and/or adjusted. Alternatively or additionally, a variable delay and/or switch delay bank 1374 component controls and/or adjusts the delay between injected pulses.

Diodes 1351 selected to prevent backflow of signals, for example, reflections returning to the pulse generator.

A circulator 1373 that directs output (i.e., generated probing pulse) of pulse generator 1371 into apparatus 1372, and directs output (i.e., reflections of the injected probing signal) of apparatus 1372 into a gate 1373.

Gate 1373 selects one or more desired reflections according to an estimated delay corresponding to a certain impedance disturbance, as described herein.

The process of injecting a pulse and isolating one or more reflection may be iterated. For each iteration, and integrator 1375 integrates each selected reflections corresponding to the same certain impedance disturbance.

An A/D component 1377 may receive each summed value (of multiple reflections from the same impedance disturbance).

A processor 1378 may receive the output of the A/D component 1377 and compute the impedance value for each impedance disturbance according to the sum of the reflections from the respective impedance disturbance, as described herein.

A monitor 1379 may displays the impedance values computed for each one of the impedance elements $Z_0, Z_1 \ldots Z_{N-1}$, for example, as numerical values and/or as a bar graph.

Various embodiments and aspects of the present invention as delineated hereinabove and as claimed in the claims section below find calculated support in the following prophetic example.

EXAMPLES

Reference is now made to the following prophetic example, which together with the above descriptions illustrate at least some implementations of the systems, apparatus, method, and/or code instructions described herein, in a non-limiting fashion.

Figure 14:
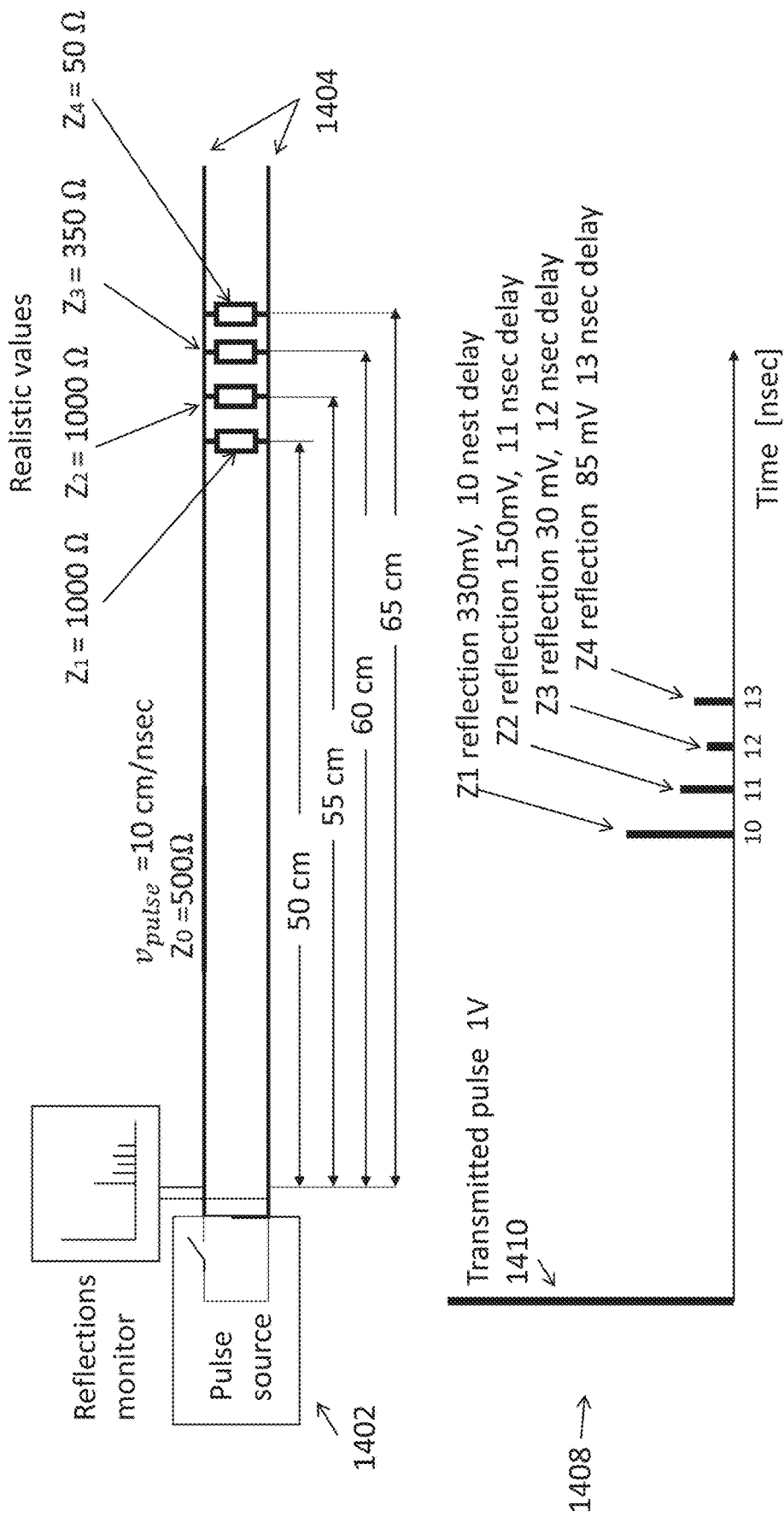
FIG. 14 is a schematic of an exemplary system for sensing impedance values in a body of the patient based on a transmitted pulse, in accordance with some embodiments of the present invention.

Reference is now made to FIG. 14, which is a schematic of an exemplary system for sensing impedance values in a body of the patient based on a transmitted pulse, in accordance with some embodiments of the present invention. A pulse source 1402 is connected to a pair of transmission lines 1404, to which four impedance disturbances (e.g., elements, resistors, fluid, tissue) are connected $Z_1$, $Z_2$, $Z_3$, $Z_4$, as described herein. Measured impedance values are presented on a display 1406, as described herein.

The following vales are defined:

The characteristic impedance of transmission line 1404, denoted $Z_0$ is 500Ω.

The estimated velocity of the pulse injected by pulse source 1402 is 10 centimeters (cm) per nanosecond (nsec).

The values of the impedance disturbances computed based on at least some of the systems, methods, apparatus, and/or code instructions described herein are: $Z_1=1000\Omega$, $Z_2=1000\Omega$, $Z_3=350\Omega$, $Z_4=50\Omega$.

The distances from each impedance disturbance from pulse source 1402, along transmission lines 1404 are: $Z_1=50$ centimeters (cm), $Z_2=55$ cm, $Z_3=60$ cm, $Z_4=65$ cm.

Graph 1408 graphically presents measured results of the reflected signals used to compute the impedance values of the impedance disturbances. The x-axis of the graph denotes time (in nsec) denoting delay of each received reflection relative to the transmitted pulse. The y-axis denotes voltages. Transmitted pulse 1410 is defined at time=0, and has a voltage of 1 volt (V). Z1 reflection is received at time 10 nsec, and has a voltage of 330 mV. Z2 reflection is received at time 11 nsec, and has a voltage of 150 mV. Z3 reflection is received at time 12 nsec, and has a voltage of 30 mV. Z4 reflection is received at time 13 nsec, and has a voltage of 85 mV.

The net reflection takes into account the fact that reflections are attenuated on the way back by former impedances.

Reference is now made to FIG. 15, which is a table depicting computation of the impedance values based on the reflected pulses, for the prophetic experimental set-up of FIG. 14, in accordance with some embodiments of the present invention.

It is noted that the sequence of computation is:

$$V_i \rightarrow r_i \rightarrow \rho_i \rightarrow Z_i$$

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant impedance elements will be developed and the scope of the term impedance element is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for measuring impedance at a plurality of locations within a body of a patient, comprising:
    an elongated probe sized and shaped that when in use is disposed within a cavity of the body of the patient or in an extracorporeal position;
    at least one pair of parallel transmission wires disposed along a length of the elongated probe,
    wherein each pair of parallel transmission wires is connected to a plurality of impedance elements at a respective spaced apart location along the length of the elongated probe in a ladder shape,
    wherein for each respective impedance element of the plurality of impedance elements, a first portion of the respective impedance element is connected to a first transmission wire of a respective pair of parallel transmission wires, and a second portion of the respective impedance element is connected to a second transmission wire of the respective pair of parallel transmission wires;
    a transmitter that injects an electrical signal to each pair of parallel transmission wires;
    a receiver that measures, for each pair of parallel transmission wires, a plurality of reflections of the electrical signal from the plurality of said impedance elements of the respective pair of parallel transmission wires; and
    a processor that computes, for each pair of parallel transmission wires, a respective impedance value for each of the impedance elements at each corresponding spaced apart location according to the measured plurality of reflections of the respective pair of parallel transmission wires.

2. The system of claim 1, wherein the processor establishes an impedance value baseline for each of the plurality of impedance elements according to the respective computed impedance value, the transmitter sequentially injects the electrical signal and the receiver iteratively measures the plurality of reflections of the electrical signals by the plurality of impedance elements, and the processor monitors for changes relative to the baseline of each of the plurality of impedance elements.

3. The system of claim 1, wherein the elongated probe comprises a naso/orogastric tube that when in use is disposed within the esophagus of the patient at least a distal end thereof is in the stomach lumen of a patient while at least one segment thereof is in the esophagus, wherein the naso/orogastric tube includes at least one feeding channel that conducts a feeding content within at least one feeding opening located in the distal end, wherein the processor performs at least one of: (i) monitoring for impedance values indicative of reflux in the esophagus, (ii) monitoring for impedance values indicative of displacement of the naso/orogastric tube within the esophagus and tracking location of the naso/orogastric tube, (iii) generating instructions for execution by an enteral feeding controller that pauses the enteral feeding when the impedance values indicative of reflux in the esophagus are detected.

4. The system of claim 1, wherein the injected signal comprises a reference harmonic signal having a selected frequency, and the processor computes the impedance value for each of the impedance elements according to a frequency domain analysis of the plurality of reflections.

5. The system of claim 4, wherein the reference harmonic signal is a sinusoidal wave.

6. The system of claim 4, wherein measuring the plurality of reflections of the electrical signal from each of the plurality of impedance elements comprises mixing the plurality of reflections with a complement of the injected reference harmonic signal for eliminating or significantly reducing a radiofrequency (RF) component to identify the intermediate frequency (IF) component which is a function of one of the measured impedance values corresponding to a selected impedance element, and computing an inversion of the IF component to compute the impedance value corresponding to the selected impedance element.

7. The system of claim 6, wherein the selected impedance element is identified according to an analysis of a phase shift of the plurality of reflections relative to the electrical signals, the phase shift being a function of a location of the selected impedance element.

8. The system of claim 6, wherein the mixing the plurality of reflections with the reference harmonic signal is iterated for each reference harmonic signal corresponding to one of a plurality of injected signal frequencies and corresponding to each of the plurality of impedance elements, to compute the impedance value corresponding to each respective impedance element.

9. The system of claim 6, wherein the IF component denotes a Discrete Fourier Transform (DFT) of the reflected signal, and wherein the reflected signal is computed by computing an Inverse Discrete Fourier Transform (IDFT) of the IF component.

10. The system of claim 1, wherein measuring the plurality of reflections of the electrical signal from each of the plurality of impedance elements comprises computing a spectral response of the plurality of impedance elements to each one of a plurality of harmonic injected signals each having a respective frequency, and computing an inverse of the spectral response.

11. The system of claim 1, wherein the injected electrical signal comprises a single pulse of a selected pulse width, and the processor computes the impedance value for each of the impedance elements according to a time domain analysis of the plurality of reflections.

12. The system of claim 11, wherein measuring comprises measuring a sequence of reflected time spaced pulses denoting reflections of the single pulse from each of the plurality of impedance element.

13. The system of claim 12, wherein the receiver sequentially selects one reflected signal at a time from the sequence of reflected time spaced pulses corresponding to a certain impedance element, wherein the impedance value is computed for the certain impedance element corresponding to the selected reflected signal, wherein the selected reflected signal is selected by a timing gate according to a computed delay corresponding to an estimated amount of time for the single pulse to travel to the certain impedance element and for the selected reflected signal to travel back to a receiver, wherein the impedance value is estimated based on the selected reflected signal.

14. The system of claim 13, wherein the single pulse is sequentially injected, and wherein during each iteration reflected signal is selected corresponding to the certain impedance element and integrated to compute a built-up signal, wherein the impedance value of the certain impedance element is computed according to the built-up signal.

15. The system of claim 1, wherein the first and second portions of the plurality of impedance elements are electrically un-insulated portions of each parallel transmission wire of each respective pair of parallel transmission wires, and portions of each pair of parallel transmission wires located between the plurality of impedance elements are electrically insulated.

16. The system of claim 1, wherein the elongate probe includes a plurality of recesses each extending within a wall thereof and corresponding to one of the plurality of impedance elements.

17. A system for measuring impedance at a plurality of locations within a body of a patient, comprising:
   an elongated probe sized and shaped that in use is disposed within a cavity of the body of the patient or in an extracorporeal position;
   at least one pair of parallel transmission wires disposed along a length of the elongated probe, wherein each parallel transmission wire of each pair of parallel transmission wires includes a plurality of alternatively electrical insulated portions and electrically non-insulated portions to create a plurality of spaced apart pairs of non-insulated wire portions;
   a transmitter that injects an electrical signal to each pair of parallel transmission wires;
   a receiver that measures, for each pair of parallel transmission wires, a reflection of the electrical signal from each of the plurality of pairs of non-insulated wire portions of the respective pair of parallel transmission wires; and
   a processor that computes, for each pair of parallel transmission wires, a respective impedance value for each of the plurality of pairs of non-insulated wire portions at each corresponding spaced apart location according to the corresponding measured reflections from each respective pair of parallel transmission wires.

18. The system of claim 17, wherein the processor further establishes an impedance value baseline for each of the plurality of pairs of non-insulated wire portions according to the respective computed impedance values, and the transmitter iteratively injects the electrical signal and the receiver iteratively measures the reflection of the electrical signal from each of the plurality of pairs of non-insulated wire portions, and the processor monitors for statistically significant changes relative to the baseline of each of the plurality of pairs of non-insulated wire portions.

19. The system of claim 17, wherein the at least one pair of parallel transmission wires are embedded within a wall of the elongated probe, and the elongated probe further comprises a recess extending within the wall of the elongated probe corresponding to each pair of non-insulated wire portions, wherein both non-insulated wire portions of each pair of parallel transmission wires reside in a respective single common recess, wherein the respective portion of each pair of parallel transmission wires located between recesses are insulated by the wall of the elongated probe.

20. The system of claim 17, wherein the processor monitors for impedance values indicative of body fluid and/or tissue contacting both non-insulated wire portions of each pair of parallel transmission wires.

21. The system of claim 17, wherein the at least one pair of parallel transmission wires are disposed on an outer surface of the elongated probe, wherein the at least one pair of parallel transmission wires are coated with electrically insulating material at spaced apart locations, wherein regions of the at least one pair of parallel transmission wires not coated with the electrically insulating material denote the spaced apart pairs of non-insulated wire portions, thereby forming an impedance sensing element.

22. The system of claim 1, wherein the processor monitors impedance changes at a plurality of locations of the patient corresponding to the locations of the plurality of impedance elements according to the plurality of reflections obtained from each pair of parallel transmission wires.

23. The system of claim 1, wherein the elongated probe comprises a naso/orogastric tube that when in use is disposed within the esophagus of the patient, and wherein the processor simultaneously evaluates an amount of reflux in an esophagus and localizes the tube versus the lower esophageal sphincter according to impedance values of the plurality of impedance elements of each pair of parallel transmission wires corresponding to different locations within the body of the patient.

* * * * *